United States Patent [19]

Carlson et al.

[11] Patent Number: 4,948,801

[45] Date of Patent: Aug. 14, 1990

[54] AMINOMETHYLOXOOXAZOLIDINYL ARYLBENZENE DERIVATIVES USEFUL AS ANTIBACTERIAL AGENTS

[75] Inventors: Randall K. Carlson; Chung-Ho Park; Walter A. Gregory, all of Wilmington, Del.

[73] Assignee: E. I. du Pont de Nemours and Company, Wilmington, Del.

[21] Appl. No.: 225,809

[22] Filed: Jul. 29, 1988

[51] Int. Cl.$^5$ .................... A61K 31/44; A61K 31/47; C07D 413/10
[52] U.S. Cl. .................................. 514/307; 514/314; 514/340; 514/256; 514/277; 544/335; 546/135; 546/144; 548/229; 548/231
[58] Field of Search ................ 548/229, 231; 514/277, 514/307, 314, 340, 256; 546/275, 135, 144; 544/335

[56] References Cited

U.S. PATENT DOCUMENTS

| | | | |
|---|---|---|---|
| 3,010,873 | 11/1961 | Cavallini | 514/277 |
| 4,150,029 | 4/1979 | Dostert | 548/231 |
| 4,476,136 | 10/1984 | Dostert | 548/229 |

*Primary Examiner*—Christine M. Nocker
*Assistant Examiner*—Frederick F. Tsung

[57] ABSTRACT

Novel aminomethyloxooxazolidinyl arylbenzene derivatives, wherein the aryl includes the phenyl, substituted phenyl, pyridyl, and substituted pyridyl groups, such as (l)-N-{3-[4-(4'-pyridyl)phenyl]-2-oxooxazolidin-5-ylmethyl}acetamide, possess useful antibacterial activity.

26 Claims, No Drawings

//4,948,801

AMINOMETHYLOXOOXAZOLIDINYL ARYLBENZENE DERIVATIVES USEFUL AS ANTIBACTERIAL AGENTS

TECHNICAL FIELD

This invention relates to aminomethyloxooxazolidinyl arylbenzene derivatives, their preparation, to pharmaceutical compositions containing them, and to methods of using them to alleviate bacterial infections.

BACKGROUND OF THE INVENTION

At the present time, no existing antibacterial product provides all features deemed advantageous for such a product. There is continual development of resistance by bacterial strains. A reduction of allergic reactions and of irritation at the site of injection, and greater biological half-life (i.e., longer in vivo activity) are currently desirable features for antibacterial products.

U.S. Pat. No. 4,128,654 issued to Fugitt et al. on Dec. 5, 1978, discloses, among others, compounds of the formula:

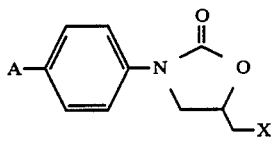

where
A=$RS(O)_n$;
X=Cl, Br or F;
R=$C_1$-$C_3$ alkyl; and
n=0, 1 or 2.
The compounds are disclosed as being useful in controlling fungal and bacterial diseases of plants.

U.S. Pat. No. 29,607 reissued Apr. 11, 1978 discloses derivatives of 5-hydroxymethyl-3-substituted-2-oxazolidinones of the formula:

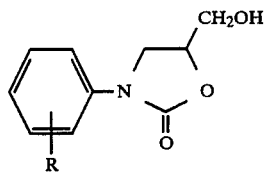

where R is H, F, $CH_3$, or $CF_3$. Such compounds are described as having antidepressive, tranquilizing, sedative, and antiinflammatory properties.

U.S. Pat. No. 4,250,318, which was issued on Feb. 10, 1981, discloses antidepressant compounds of the formula:

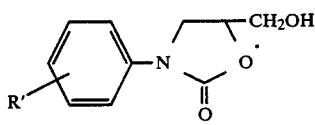

where R' can be, among others, a para-n-pentylamino group, an $SR_1$ group where $R_1$ is $C_1$-$C_5$ alkyl, or an acetylmethylthio group.

U.S. Pat. No. 4,340,606, issued to Fugitt et al. on Jul. 20, 1982, discloses antibacterial agents of the general formula:

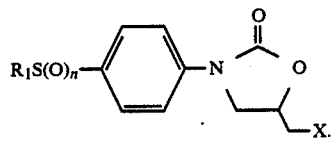

where
$R_1$=$CH_3$, $C_2H_5$, $CF_2H$, $CF_3$ or $CF_2CF_2H$; and
X=$OR_2$ ($R_2$=H or various acyl moieties).

U.S. Pat. No. 3,687,965, issued to Fauran et al. on Aug. 29, 1972, discloses compounds of the formula:

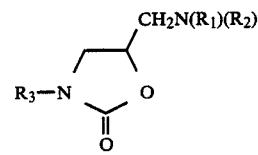

where
—N($R_1$)($R_2$) represents either dialkylamino radical in which the alkyl portions have one to five carbon atoms, or a heterocyclic amino radical which may be substituted by an alkyl radical having one to five carbon atoms or by a pyrrolidinocarbonylmethyl radical, and
$R_3$ represents a phenyl radical which may be substituted by one or more of the following radicals:
an alkoxy radical having one to five carbon atoms;
a halogen atom;
a trifluoromethyl radical, or
a carboxyl radical which may be esterified.
The patent states that these compounds possess hypotensive, vasodilatatory, spasmolytic, sedative, myorelaxant, analgesic and antiinflammatory properties. There is no mention of antibacterial properties.

Belgian Patent 892,270, published Aug. 25, 1982, discloses monoamine oxidase inhibitors of the formula

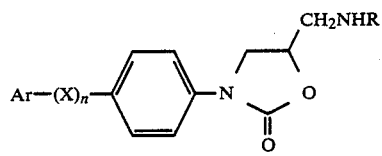

where
R is H, $C_1$-$C_4$ alkyl or propargyl;
Ar is phenyl, optionally substituted by halo or trifluoromethyl;
n is 0 or 1; and
X is —$CH_2CH_2$—, —CH=CH—, an acetylene group or —$CH_2O$—.

U.S. Pat. No. 4,461,773 issued to W. A. Gregory on Jul. 24, 1984 discloses antibacterial agents of the formula

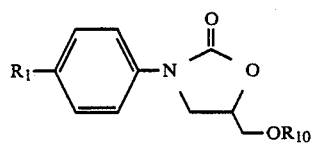

wherein, for the l, and mixtures of the d and l stereoisomers of the compound, $R_1$ is $R_2SO_2$,

$R_2$ is $-NR_3R_4$, $-N(OR_3)R_4$, $-N_3$, $-NHNH_2$, $-NX_2$, $-NR_6X$, $-NXZ$,

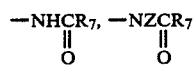

or $-N=S(O)_nR_8R_9$;

$R_3$ and $R_4$ are independently H, alkyl of 1-4 carbons or cycloalkyl of 3-8 carbons;

$R_5$ is $NR_3R_4$ or $OR_3$;

$R_6$ is alkyl of 1-4 carbons;

$R_7$ is alkyl of 1-4 carbons, optionally substituted with one or more halogens;

$R_8$ and $R_9$ are independently alkyl of 1-4 carbons or, taken together are $-(CH_2)_p-$;

$R_{10}$ is H, alkyl of 1-3 carbons,

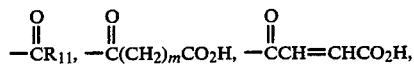

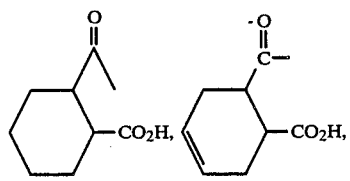

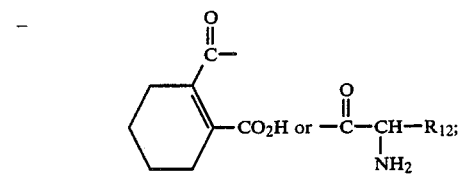

$R_{11}$ is alkyl of 1-12 carbons;
$R_{12}$ is H, alkyl of 1-5 carbons, $CH_2OH$ or $CH_2SH$;
X is Cl, Br or I;
Z is a physiologically acceptable cation;
m is 2 or 3;
n is 0 or 1; and
p is 3, 4 or 5;
and when $R_{10}$ is alkyl of 1-3 carbons, $R_1$ can also be $CH_3S(O)_q$ where q is 0, 1 or 2;
or a pharmaceutically acceptable salt thereof.

U.S. Pat. No. 4,705,799 issued to Gregory on Nov. 10, 1987 discloses antibacterial agents of the formula:

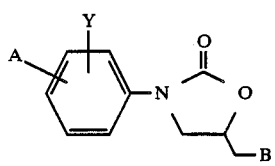

wherein,
for the l, and mixtures of the d and l stereoisomers of the compound,

A is $-NO_2$, $-S(O)_nR_1$, $-S(O)_2-N=S(O)_pR_2R_3$, $-SH$,

$-COR_{23}$, $-COR_{25}$, $-CONR_5R_6$,

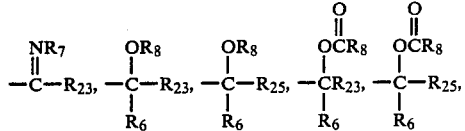

$-CN$, $-OR_5$, halogen, $-NR_5R_6$,

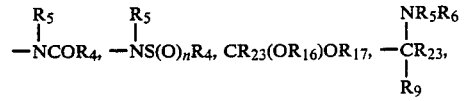

alkyl of 1 to 8 carbons, optionally substituted with one or more halogen atoms, OH, $=O$ other than at alpha position, $S(O)_nR_{24}$, $NR_5R_6$, alkenyl of 2-5 carbons, alkynyl of 2-5 carbons or cycloalkyl of 3-8 carbons;

$R_1$ is
$C_1-C_4$ alkyl, optionally substituted with one or more halogen atoms, OH, CN, $NR_5R_6$ or $CO_2R_8$; $C_2-C_4$ alkenyl; $-NR_9R_{10}$; $-N_3$;

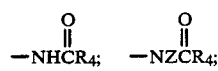

$-NX_2$; $NR_9X$ $-NXZ^+$;

$R_2$ and $R_3$ are independently $C_1-C_2$ alkyl or, taken together are $-(CH_2)_q-$;

$R_4$ is alkyl of 1-4 carbons, optionally substituted with one or more halogens;

$R_5$ and $R_6$ are independently H, alkyl of 1-4 carbons or cycloalkyl of 3-8 carbons;

$R_7$ is $-NR_5R_6$, $-OR_5$ or

$R_8$ is H or alkyl of 1-4 carbons;
$R_9$ is H, $C_1-C_4$ alkyl or $C_3-C_8$ cycloalkyl;
$R_{10}$ is H, $C_1-C_4$ alkyl, $C_2-C_4$ alkenyl, $C_3-C_4$ cycloalkyl, $-OR_8$ or $-NR_{11}R_{114}$;
$R_{11}$ and $R_{114}$ are independently H or $C_1-C_4$ alkyl, or taken together, are $-(CH_2)_r-$;
X is Cl, Br or I;
Y is H, F, Cl, Br, alkyl of 1-3 carbons, or $NO_2$, or A and Y taken together can be $-O-(CH_2)_tO-$;
Z is a physiologically acceptable cation;
n is 0, 1 or 2;
p is 0 or 1;
q is 3, 4 or 5;
r is 4 or 5;
t is 1, 2 or 3;
B is $-NH_2$,

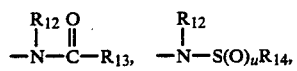

or N₃;

$R_{12}$ is H, $C_1$-$C_{10}$ alkyl or $C_3$-$C_8$ cycloalkyl;

$R_{13}$ is H; $C_1$-$C_4$ alkyl optionally substituted with one or more halogen atoms; $C_2$-$C_4$ alkenyl; $C_3$-$C_4$ cycloalkyl; phenyl; —CH²OR₁₅; —CH(OR₁₆)OR₁₇; —CH₂-S(O)ᵥR₁₄;

—OR₁₈; —SR₁₄; —CH₂N₃; the aminoalkyl groups derived from α-amino acids such as glycine, L-alanine, L-cysteine, L-proline, and D-alanine; —NR₁₉R₂₀; or C(NH₂)R₂₁R₂₂;

$R_{14}$ is $C_1$-$C_4$ alkyl, optionally substituted with one or more halogen atoms;

$R_{15}$ is H or $C_1$-$C_4$ alkyl, optionally substituted with one or more halogen atoms;

$R_{16}$ and $R_{17}$ are independently $C_1$-$C_4$ alkyl or, taken together, are —(CH₂)ₘ—;

$R_{18}$ is $C_1$-$C_4$ alkyl or $C_7$-$C_{11}$ aralkyl;

$R_{19}$ and $R_{20}$ are independently H or $C_1$-$C_2$ alkyl;

$R_{21}$ and $R_{22}$ are independently H, $C_1$-$C_4$ alkyl, $C_3$-$C_6$ cycloalkyl, phenyl or, taken together, are —(CH₂)ₛ—;

u is 1 or 2;
v is 0, 1 or 2;
m is 2 or 3;
s is 2, 3, 4 or 5; and $R_{23}$ is H, alkyl of 1-8 carbons optionally substituted with one or more halogens, or cycloalkyl of 3-8 carbons;

$R_{24}$ is alkyl of 1-4 carbons or cycloalkyl of 3-8 carbons;

$R_{25}$ is alkyl of 1-4 carbons substituted with one or more of —S(O)ₙR₂₄, —OR₈,

—NR₅R₆, or alkenyl of 2-5 carbons optionally substituted with CHO; or a pharmaceutically suitable salt thereof; provided that:

(1) when A is CH₃S—, then B is not

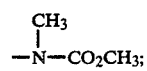

(2) when A is CH₃SO₂—, then B is not

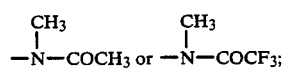

(3) when A is H₂NSO₂— and B is

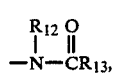

then $R_{12}$ is H;

(4) when A is —CN, B is not —N₃;

(5) when A is (CH₃)₂CH, B is not NHCOCH₂Cl;

(6) when A is OR₅, then B is not NH₂;

(7) when A is F, then B is not NHCO₂CH₃.

None of the above-mentioned references suggest the novel antibacterial compounds of this invention.

SUMMARY OF THE INVENTION

According to the present invention, there is provided an arylbenzene oxazolidinone of the formula:

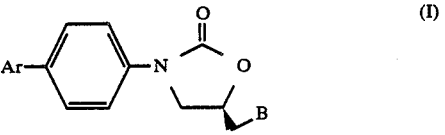

wherein, for the l, and mixtures of the d and l stereoisomers of the compound

Ar is an aromatic group selected from the group consisting of

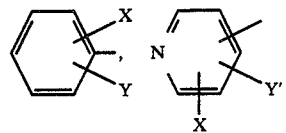

diazinyl group optionally substituted with X and Y, a triazinyl group optionally substituted with X and Y,

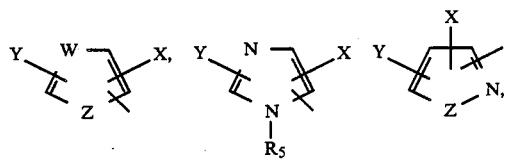

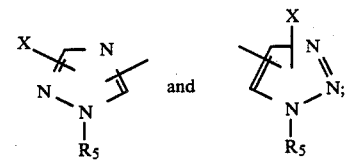

Z is O, S, or NR₅;
W is CH or N, or also can be S or O when Z is NR₅;
X independently is H, —NO₂, —S(O)ₙR₁, tetrazoyl,

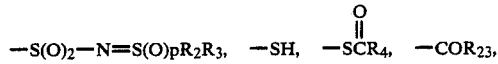

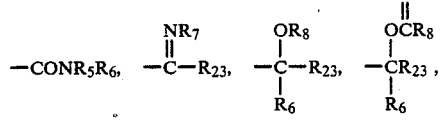

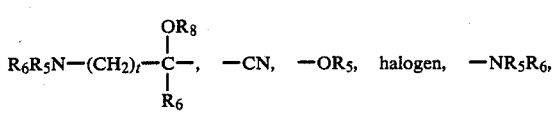

-continued

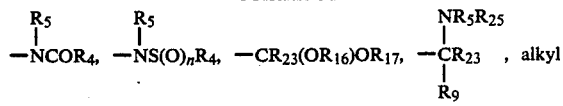

of 1 to 8 carbons optionally substituted with one or more halogen atoms, OH, =O other than at alpha position, $S(O)_nR_{24}$, or $NR_5R_6$, alkenyl of 2-5 carbons or cycloalkyl of 3-8 carbons;

$R_1$ is $C_1-C_4$ alkyl, optionally substituted with one or more halogen atoms, OH, CN, $NR_5R_6$ or $CO_2R_8$; $C_2-C_4$ alkenyl; $-NR_9R_{10}$; $-N_3$;

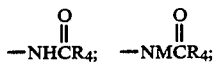

$-NG_2$; $NR_9G-\overset{-}{\ }NGM^+$;

$R_2$ and $R_3$ are independently $C_1-C_2$ alkyl or, taken together are $-(CH_2)_q-$;

$R_4$ is alkyl of 1-4 carbons, optionally substituted with one or more halogens;

$R_5$ and $R_6$ are independently H, alkyl of 1-8 carbons, cycloalkyl of 3-8 carbons $-(CH_2)_tOR_8$, $-(CH_2)_tNR_{11}R_{11a}$, or taken together are $-(CH_2)_2O(CH_2)_2-$, $-(CH_2)_tCH(COR_4)-$, or

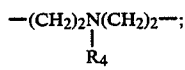

$R_7$ is $-NR_5R_6$, $-OR_5$ or

$R_8$ is H or alkyl of 1-4 carbons;
$R_9$ is H, $C_1-C_4$ alkyl or $C_3-C_8$ cycloalkyl;
$R_{10}$ is H, $C_1-C_4$ alkyl, $C_2-C_4$ alkenyl, $C_3-C_4$ cycloalkyl, $-OR_8$ or $-NR_{11}R_{11A}$;
$R_{11}$ and $R_{11A}$ are independently H or $C_1-C_4$ alkyl, or taken together, are $-(CH_2)_r-$;
G is Cl, Br or I;
Y independently is H, F, Cl, Br, $OR_8$, alkyl of 1-3 carbons, or $NO_2$;
X and Y taken together (a) when Ar is

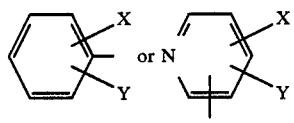

to form a fused six-membered carbocyclic ring, or (b) when Ar is

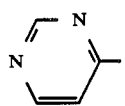

to form

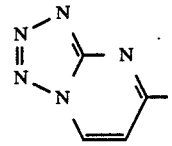

M is a physiologically acceptable cation;
n is 0, 1 or 2
p is 0 or 1;
q is 3, 4 or 5;
r is 4 or 5;
t is 1, 2 or 3;
B is $-NH_2$,

$R_{12}$ is H, $C_1-C_{10}$ alkyl or $C_3-C_8$ cycloalkyl;
$R_{13}$ is H; $C_1-C_4$ alkyl optionally substituted with one or more halogen atoms; $C_2-C_4$ alkenyl; $C_3-C_4$ cycloalkyl; phenyl; $-CH_2OR_{15}$; $-CH(OR_{16})OR_{17}$; $-CH_2S(O)_vR_{14}$;

$$-\overset{O}{\underset{\|}{C}}R_{15};$$

$-OR_{18}$; $-SR_{14}$; $-CH_2N_3$; the aminoalkyl groups derived from α-amino acids such as glycine, L-alanine, L-cysteine, L-proline, and D-alanine; $-NR_{19}R_{20}$; or $-C(NH_2)R_{21}R_{22}$;

$R_{14}$ is $C_1-C_4$ alkyl, optionally substituted with one or more halogen atoms;
$R_{15}$ is H or $C_1-C_4$ alkyl, optionally substituted with one or more halogen atoms;
$R_{16}$ and $R_{17}$ are independently $C_1-C_4$ alkyl or, taken together, are $-(CH_2)_m-$;
$R_{18}$ is $C_1-C_4$ alkyl or $C_7-C_{11}$ aralkyl;
$R_{19}$ and $R_{20}$ are independently H or $C_1-C_2$ alkyl;
$R_{21}$ and $R_{22}$ are independently H, $C_1-C_4$ alkyl, $C_3-C_6$ cycloalkyl, phenyl or, taken together, are $-(CH_2)_s-$;
u is 1 or 2;
v is 0, 1 or 2;
m is 2 or 3;
s is 2, 3, 4 or 5;
$R_{23}$ is H, alkyl of 1-8 carbons optionally substituted with one or more halogens, cycloalkyl of 3-8 carbons, alkyl of 1-4 carbons substituted with one or more of $-S(O)_nR_{24}$, $-OR_8$, $$-\overset{O}{\underset{\|}{O}}CR_8,$$

or $-NR_5R_6$; or alkenyl of 2-5 carbons optionally substituted with CHO or $CO_2R_8$;
$R_{24}$ is alkyl of 1-4 carbons or cycloalkyl of 3-8 carbons; and
$R_{25}$ is $R_6$ or $NR_5R_6$;
or a pharmaceutically suitable salt thereof; provided that:
(1) when B is $NH_2$, then Ar is not phenyl optionally substituted with halogen or $CF_3$.

When used herein, the term "a diazinyl group optionally substituted with X and Y" means the following groups:

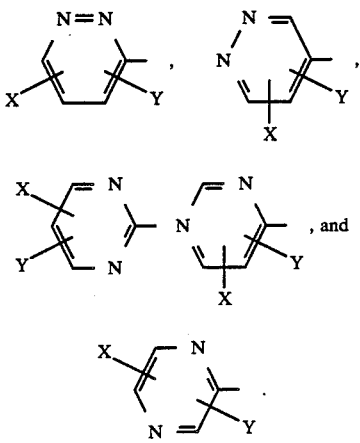

When used herein, the term "a triazinyl group optionally substituted with X and Y" means the following groups:

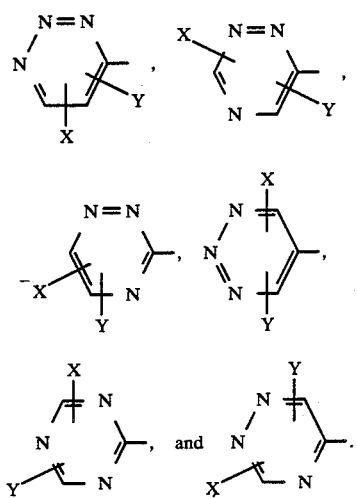

Also provided is a pharmaceutical composition consisting essentially of a suitable pharmaceutical carrier and a compound of Formula (I) and a method of using a compound of Formula (I) to treat bacterial infection in a mammal.

Further provided is a process for preparing compounds of Formula (I), such a process being described in detail hereinafter.

PREFERRED EMBODIMENTS

1. Preferred Ar groups are:

where X and Y are as defined.

More preferred Ar groups are those preferred Ar groups where Y is H.

Most preferred Ar groups are the preferred Ar groups where Y is H and X is H, alkyl of 1–5 carbon atoms, —SCH$_3$, —SOCH$_3$, —SO$_2$CH$_3$,

OR$_5$, —CH$_2$NR$_5$R$_6$, R$_6$R$_5$N(CH$_2$)$_2$CH(OH)—, or —CN.

2. A preferred B group is:

where R$_{13}$ is H, CH$_3$, —OR$_{18}$, CH$_2$Cl, CH$_2$OH, or CH$_2$OCH$_3$.

Preferred B groups are

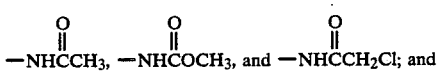

is specifically preferred.

Specifically preferred compounds are:
- (l)-N-[3-(4-phenylphenyl)-2-oxooxazolidin-5-ylmethyl]acetamide;
- (l)-N-[3-(4-(4'-acetylphenyl)phenyl)-2-oxoazolidin-5-ylmethyl]acetamide;
- (l)-N-[3-(4-(4'-methylsulfinylphenyl)phenyl)-2-oxooxazolidin-5-ylmethyl]acetamide;
- (l)-N-[3-(4-(4'-methylsulfonylphenyl)phenyl)-2-oxooxazolidin-5-ylmethyl]acetamide;
- (l)-N-[3-(4-(4'-cyanophenyl)phenyl-2-oxooxazolidin-5-ylmethyl]acetamide;
- (l)-N-[3-(4-(4'-diethylaminomethylphenyl)phenyl)-2-oxooxazolidin-5-ylmethyl]acetamide;
- (l)-N-[3-(4-(4'-di-n-propylaminomethylphenyl)phenyl)-2-oxooxazolidin-5-ylmethyl]acetamide;
- (l)-N-[3-(4-(4'-(3-N,N-dimethylamino-1-hydroxypropyl)phenyl)phenyl)-2-oxooxazolidin-5-ylmethyl]acetamide;
- (l)-N-[3-(4-(4'-(1-hydroxy-3-(4-morpholinyl)propyl)phenyl)phenyl)-2-oxooxazolidin-5-ylmethyl]acetamide;
- (l)-N-[3-(4-(4'-pyridyl)phenyl)-2-oxooxazolidin-5-ylmethyl]acetamide, hydrochloride;
- (l)-N-[3-(4-(3'-pyridyl)phenyl)-2-oxooxazolidin-5-ylmethyl]acetamide, hydrochloride.

DETAILED DESCRIPTION

The compounds of Formula (I) contain at least one chiral center, and as such exist as two individual isomers or as a mixture of both. This invention relates to the levorotatory isomer (l) which for many of the compounds in this invention can be referred to as the (S) isomer, as well as mixtures containing both the (d) or (R) and (S) isomers. Additional chiral centers may be present in the groups Ar and/or B; and this invention relates to all possible stereoisomers in these groups.

For the purpose of this invention, the l-isomer of compounds of Formula (I) is intended to mean compounds of the configuration depicted; when B is NHAc, and closely related groups, this isomer is described as the (S)-isomer in the Cahn-Ingold-Prelog nomenclature:
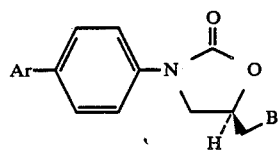
SYNTHESIS
Compounds of Formula (I) can be prepared as follows:
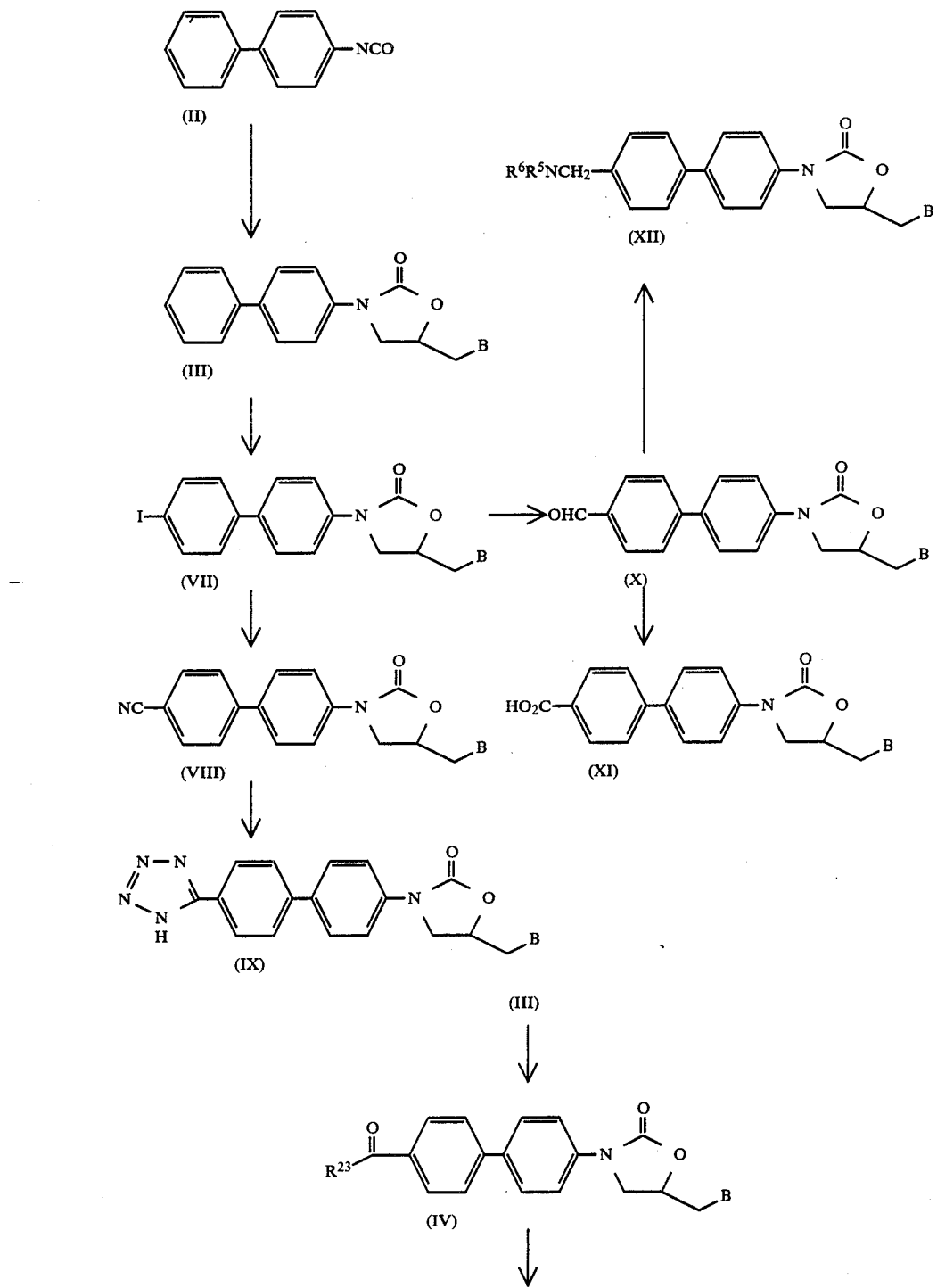

-continued
Scheme 1
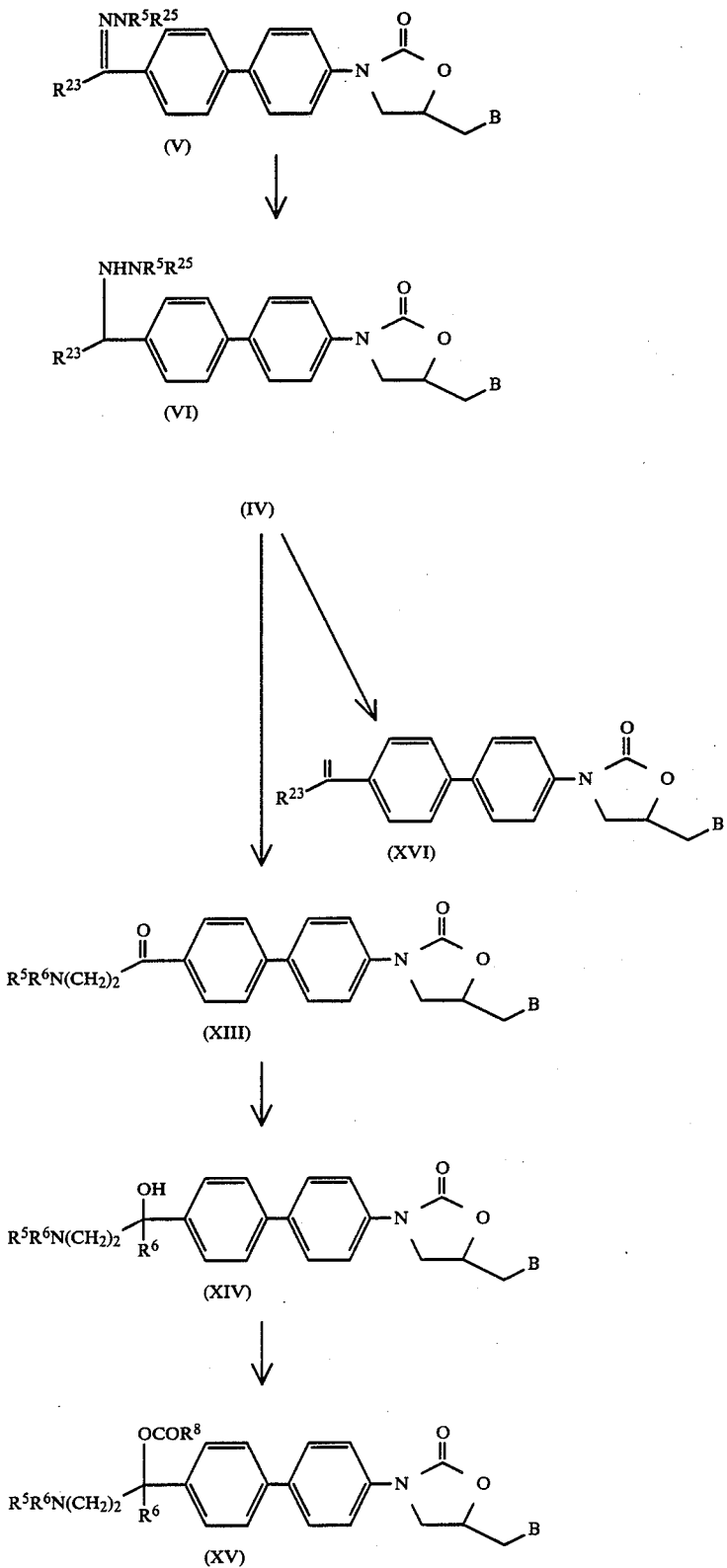

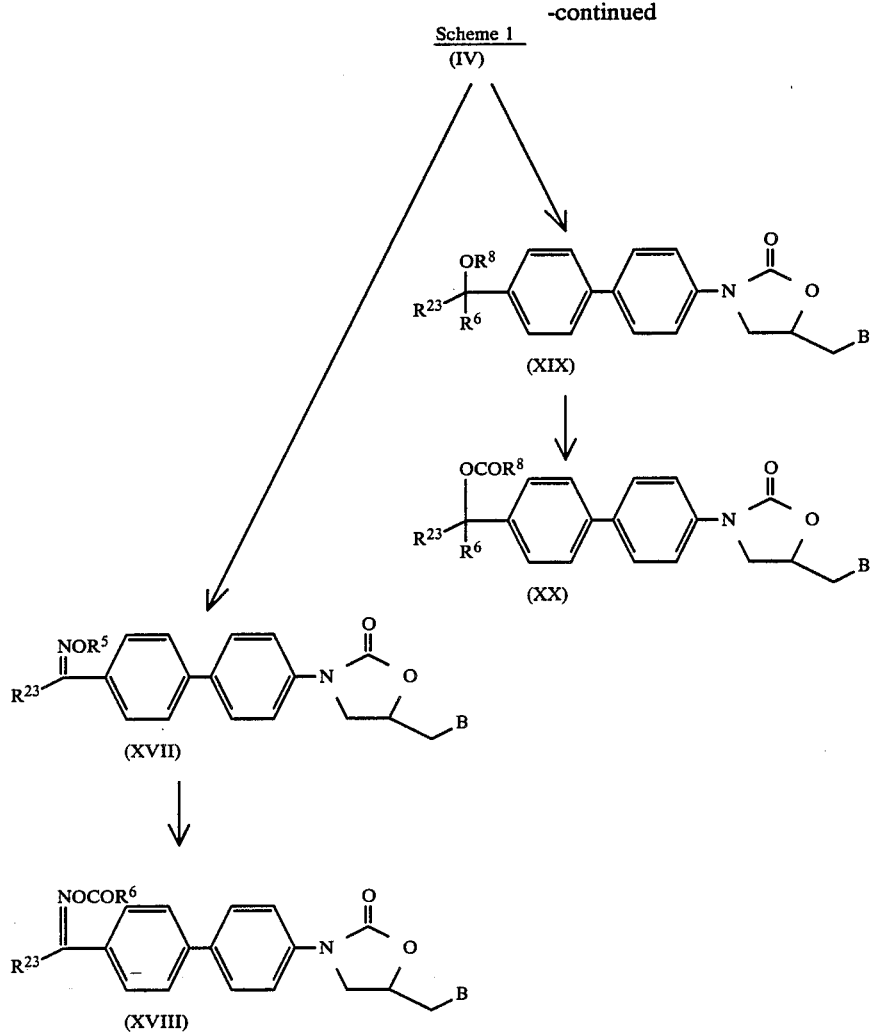

In Scheme 1, $R_{23}$ is H or alkyl of 1–8 carbons optionally substituted with a halogen or a terminal carboxylic acid or its salts. $R_5$, $R_6$, and B are as described previously. $R_8$ is H or alkyl of 1–4 carbons optionally substituted with a terminal carboxylic acid or its salts.

The compound (II) is converted to a compound of Formula (III) according to the process exactly paralleling that which was previously described in U.S. Pat. No. 4,705,799. The B groups in Formula (I) can be selected from a variety of groups described and prepared according to the procedures disclosed in the above patent.

A compound of Formula (III) is acylated with acetic anhydride, propionic anhydride, chloroacetic anhydride or succinic anhydride also according to the process described in the aforesaid patent to give a compound of Formula (IV). Reaction of a compound of Formula (IV) with a substituted hydrazine in a solvent such as ethanol, methanol or THF at 20° C. to under refluxing temperature of the solvent chosen gives a hydrazone of Formula (V), which can be reduced to a hydrazine derivative of Formula (VI) by reduction using a borohydride such as sodium cyanoborohydride in methanol at 25° to 55° C.

A compound of Formula (III) is iodinated with iodine monochloride in an acetic acid-trifluoroacetic acid mixture at 40° to 70° C. to a compound of Formula (VII), which can be converted to a cyano compound of Formula (VIII) by reaction with cuprous cyanide. The cyano group of a compound of (VIII) can be converted to a tetrazole derivative of Formula (IX) by reaction with trimethylsilyl azide in DMF at 120°–145° C. An iodocompound (VII) can also be converted to an aldehyde of Formula (X) by addition of carbon monoxide in a suitable solvent such as THF, glyme and DMF or mixtures thereof at 40° to 70° C. in the presence of a catalyst such as tributyltin hydride and tetrakis(triphenylphosphine)palladium(0). An aldehyde of (X) can be converted to the corresponding carboxylic acid of Formula (XI) by oxidation with variety of oxidants such as chromic acid. An aldehyde of (X) can also be reductively aminated with an alkylamine such as diethylamine, ethylmethylamine or methylpiperidine in an alcoholic solvent using a reducing agent such as sodium cyanoborohydride and zinc chloride at 0° to 35° C. to give an amine of Formula (XII).

Mannich reaction of a ketone of Formula (IV) with variety of alkylamines previously described gives a Mannich base of Formula (XIII) which can be reduced to an alcohol of Formula (XIV) with a borohydride reducing agent such as sodium cyanoborohydride in methanol. An alcohol of Formula (XIV) can be converted to a half ester of a dibasic acid of Formula (XV) by treatment with a dibasic acid anhydride such as succinic or glutaric anhydrides. When the Mannich reaction is carried out with a ketone of Formula (IV), where $R_{23}$ is ethyl, with dimethylamine, an unsaturated ketone of Formula (XVI) is also obtained.

A ketone of Formula (IV), when reacted with an hydroxylamine or a carboxymethyloxyamine in ethanol in the presence of pyridine, produces the corresponding oxime of Formula (XVII). An oxime of Formula (XVII) can be converted to the oximino half ester of a dibasic carboxylic acid of Formula (XVIII) by reaction with a dibasic acid anhydride such as succinic and glutaric anhydrides.

A ketone or aldehyde of Formulae (IV) and (X) can be reduced to a corresponding alcohol of Formula (XIX) by a reducing agent such as sodium borohydride. An alcohol of Formula (XIX) can be esterified with a mono- or dibasic acid anhydride to give a corresponding ester of Formula (XX).

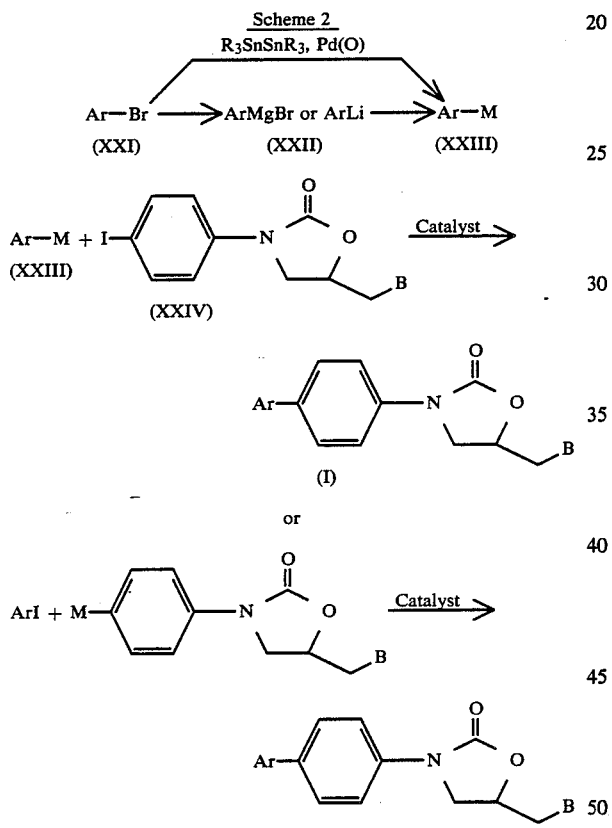

As shown in Scheme 2, Ar is as described previously provided that it contains no active hydrogen, (i.e., no NH, OH or SH), M is a zinc chloride, trialkyltin or boronic acid radical and the catalyst can be selected from one of the many palladium or nickel coordination compounds such as bis(triphenylphosphine)palladium-(II) chloride, tri(2-tolyl)phosphine and palladium(II) acetate, or bis(triphenylphosphine)nickel(II) chloride. An aromatic bromide of Formula (XXI) is converted to a corresponding Grignard reagent with magnesium or to a lithium reagent with alkyllithium by the usual procedures which are well known in the art. A reagent of Formula (XXII) is converted to an organozinc chloride compound with zinc chloride, to a trialkyltin compound with trialkyltin chloride or to a boronic acid with triisopropylborate, each followed by basic hydrolysis in a suitable solvent such as ether, THF or glyme. Alternatively, when Ar contains active hydrogens, an organotin compound of Formula (XXIII) can be prepared by a palladium catalyzed reaction with a bistrialkyltin reagent. A resulting organometallic compound of Formula (XXIII) is cross coupled with a 3-(4-iodophenyl)-2-oxooxazolidin-5-ylmethyl derivative of Formula (XXIV) in a suitable solvent such as THF or DMF in the presence of a catalyst usually selected from those previously described. The cross coupling reaction works equally well when an aryliodide and a 3-(4-trialkylstannylphenyl)-2-oxooxazolidinyl derivative is reacted in the same manner. The iodo compound of Formula (XXIV) is prepared by iodinating (l)-N-(3-phenyl-2-oxooxazolidin-5-ylmethyl)acetamide using iodine and silver trifluoroacetate or iodine monochloride in a solvent such as chloroform, acetonitrile, acetic acid or mixtures of solvents thereof at a temperature of 0° to 60° C., followed by normal work-up procedures.

Another coupling reaction, although limited in its applicability, can be used to prepare a compound of Formula (I) where Ar is a dihydroxyphenyl as described in synthetic Scheme 3.

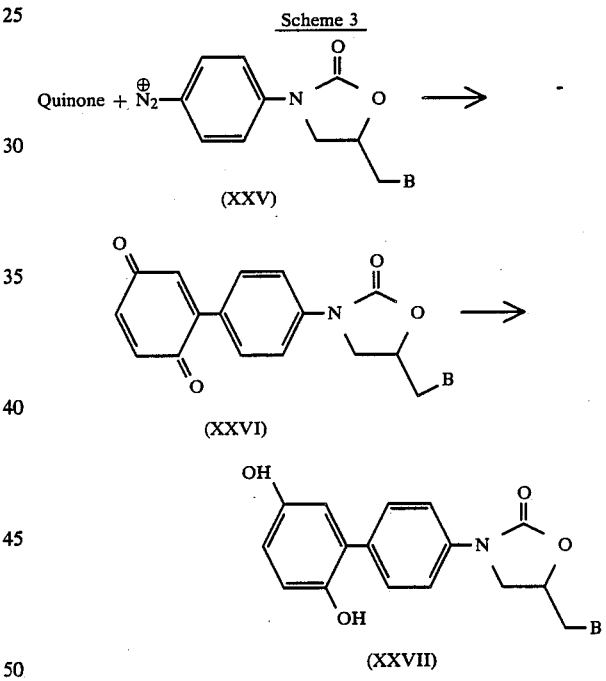

Quinone is reacted with a diazonium salt (XXV) prepared from a 3-(4-aminophenyl)-2-oxooxazolidin-5-ylmethyl derivative to give an adduct of Formula (XXVI), which can be reduced with a borohydride reducing agent such as sodium borohydride to give a dihydroxy compound of Formula (XXVII). The hydroxy groups can be converted to the corresponding ethers using conventional techniques.

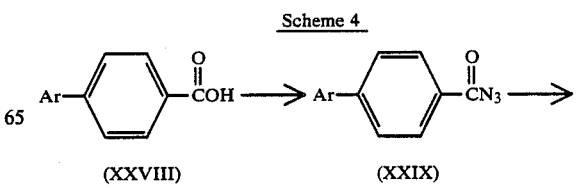

-continued
Scheme 4

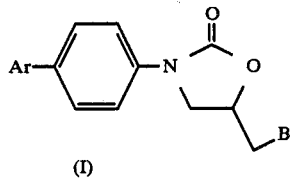

(I)

Synthetic Scheme 4 is widely applicable to prepare most of the compounds of Formula (I) provided that there are no active hydrogen atoms (i.e., no NH, OH or SH) present in Ar as described previously. Compounds containing these excluded groups can be prepared via Schemes 1, 3 or 5. A compound of Formula (XXVIII) can be prepared in variety of ways. For example, many of such compounds can be prepared by procedures described in D. J. Byron, G. W. Gray and R. C. Wilson, J. Chem. Soc. (C), 840 (1966). A compound of Formula (XXVIII) can be converted to the corresponding acid chloride followed by reaction with sodium azide according to standard organic reaction procedures to a compound of Formula (XXIX). A compound of Formula (XXIX) is then employed in place of the compound of Formula (II) in Scheme 1 to give the compound of Formula (I).

Scheme 5

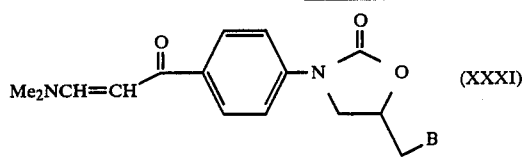 (XXXI)

↑ (MeO)$_2$CHNMe$_2$

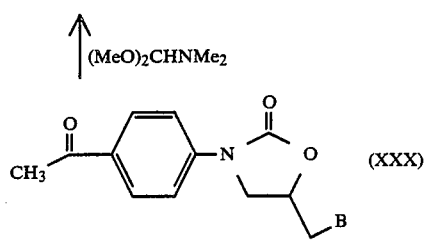 (XXX)

↓ Br$_2$/CHCl$_3$

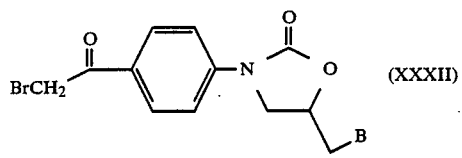 (XXXII)

(XXXI)

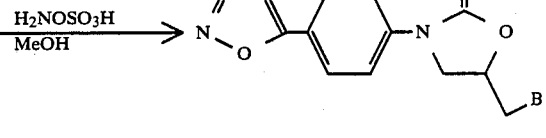

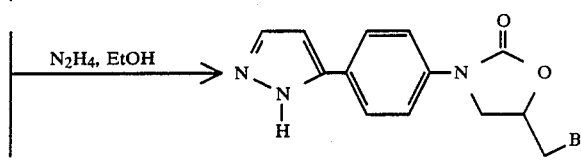

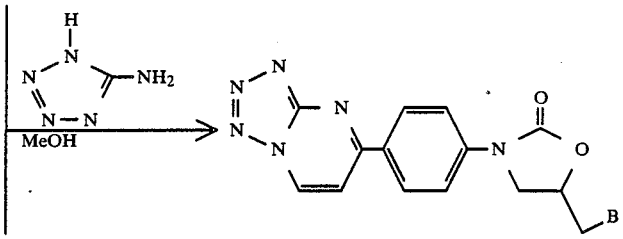

-continued

Scheme 5

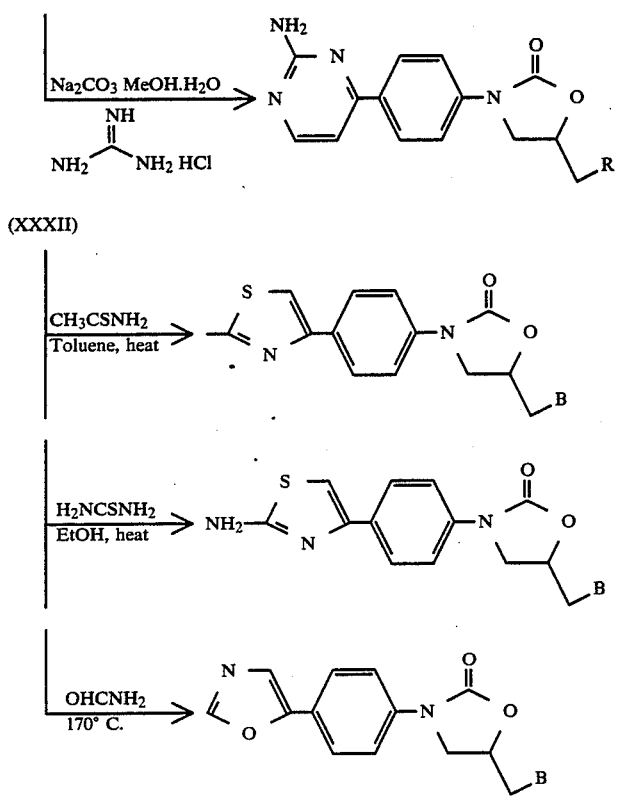

(XXXII)

Compounds of Formula (I) which can be prepared according to the synthetic Scheme 5 are those with Ar groups made up of 5- and 6-membered ring heterocycles as illustrated.

A 3-(4-acetylphenyl)-2-oxooxazolidin-5-yl derivative (XXX) prepared according to U.S. Pat. No. 4,705,799 is converted to a compound of Formula (XXXI) by reacting it with dimethoxydimethylformamide at 100° to 120° C. Reaction of a compound of Formula (XXXI) with a variety of amines give compounds of Formula (I) where Ar is an heteroaromatic moiety as shown.

Similarly, a bromoacetyl derivative (XXXII) where B is azide ($N_3$) obtained by bromination of a compound (XXX) can be reacted with a variety of amides to produce more compounds of Formula (I) where Ar is an heteroaromatic moiety. Azides can be reduced to amines as described in U.S. Pat. No. 4,705,799.

Pharmaceutically suitable salts of compounds of Formula (I) can be prepared in a number of ways known in the art. When B is $NH_2$, pharmaceutically suitable salts include those resulting from treatment with mineral and organic acids such as acetic, hydrochloric, sulfuric, phosphoric, succinic, fumaric, ascorbic, and glutaric acids.

The invention can be further understood by reference to the following examples in which parts and percentages are by weight unless otherwise indicated.

EXAMPLE 1

Preparation of
(l)-5-Azidomethyl-3-(4-phenylphenyl)-2-oxazolidinone
(I, Ar=$C_6H_5$, B=$N_3$)

Part A: Preparation of
(l)-5-Hydroxymethyl-3-(4-phenyl phenyl)-2-oxazolidinone (I, Ar=$C_6H_5$, B=OH)

A solution containing 10 g (51.2 mmol) of 4-phenylphenylisocyanate and 7.5 g (52.0 mmol) of (l)-glycidyl butyrate in 20 mL of dry xylene was added dropwise to 160 mL of boiling dry xylene containing 0.30 g of lithium bromide and 0.75 g of tributylphosphine oxide over a period of 30 minutes. The mixture was heated under reflux for 1 hour after the addition was complete, allowed to cool to room temperature and the solvent was removed under reduced pressure. The residue was triturated with hexane and the resulting solid was dissolved in 150 mL of methanol. To this solution was added 0.7 mL of 25% sodium methoxide in methanol, stirred overnight and the white precipitate formed was collected on a filter to give 13 g (95% theory) of the desired alcohol, mp 236°–240° C., shown to be at least 99% pure by HPLC. The alcohol can be further purified by recrystallization from methanol.

Part B: Preparation of
(l)-5-Hydroxymethyl-3-(4-phenylphenyl)-2-oxazolidinone p-toluenesulfonate (I, Ar=$C_6H_5$, B=OTs)

To a solution of 12.94 g (48.05 mmol) of (l)-5-hydroxymethyl-3-(4-phenylphenyl)-2-oxazolidinone in 100 mL of dry pyridine was added 10.6 g (15% excess) of p-toluenesulfonyl chloride at 0°–5° C., and the mixture was stirred at 10°–15° C. until all of the alcohol was converted to the tosylate (Ts) as shown by HPLC analysis. The mixture was poured into 500 mL of ice water with vigorous stirring and the resulting white precipitate was collected and recrystallized from an ethanol-acetonitrile mixture to give 16.2 g of the tosylate, mp 157.5°–158.5° C.

Part C:

A mixture of 15.3 g (37.4 mmol) of (l)-5-hydroxymethyl-3-(4-phenylphenyl)-2-oxazolidinone p-toluenesulfonate, 0.2 g of 18-crown-6 and 2.7 g (41.1 mmol, 10% excess) of sodium azide in 60 mL of dry dimethylformamide (DMF) was heated at 70° C. (±5°) for 5 hours and the mixture was poured into 300 mL of ice water to give a white precipitate. The precipitate was collected on a filter to give 10.4 g of the desired azide as a colorless solid, mp 163.5°–164.5° C.

EXAMPLE 2

Preparation of
(l)-5-Aminomethyl-3-(4-phenylphenyl)-2-oxazolidinone
.(I, Ar=C$_6$H$_5$, B=NH$_2$)

(l)-5-Azidomethyl-3-(4-phenylphenyl)-2-oxazolidinone (10.4 g) suspended in 200 mL of 95% ethanol was hydrogenated in the presence of 0.7 g of platinum oxide under 40–50 psig (2.76×10$^5$–3.45×10$^5$ pascals) of hydrogen. The catalyst was removed by filtration through a celite bed, the bed was washed with tetrahydrofuran (THF) and the combined ethanol filtrate and THF washings were concentrated under reduced pressure to give 9.2 g of the desired amine as a colorless solid, mp 140°–141° C.

EXAMPLE 3

Preparation of
(l)-N-[3-(4-Phenylphenyl)-2-oxooxazolidin-5-ylmethyl]acetamide (I, Ar=C$_6$H$_5$, B=NHCOCH$_3$)

To a solution containing 9.2 g of (l)-5-aminomethyl-3-(4-phenylphenyl)-2-oxazolidinone and 8 mL of triethylamine in 200 mL of dry THF was added 3.5 mL of acetyl chloride dissolved in 10 mL of THF dropwise at 0°–10° C. The mixture was concentrated under reduced pressure and the residue was triturated with water to give a solid which was recrystallized from ethanol to give 8.7 g of the pure amide as a colorless solid, mp 226°–227° C.

Anal. Calcd for C$_{18}$H$_{18}$N$_2$O$_3$: C, 69.66; H, 5.85; N, 9.03. Found: C, 69.44; H, 5.94; N, 9.03. 69.48 5.85 9.04.

EXAMPLE 4

Preparation of
(l)-N-[3-(4-(4'-Acetylphenyl)phenyl)-2-oxooxazolidin-5-ylmethyl]acetamide (I, Ar=CH$_3$COC$_6$H$_4$, B=NHCOCH$_3$)

To 50 g of trifluoromethanesulfonic acid was added 7.5 mL of acetic anhydride dropwise at 0°–5° C. followed by 2.5 g of (l)-N-[3-(4-phenylphenyl)-2-oxooxazolidin-5-ylmethyl]acetamide. The mixture was stirred at room temperature for 3 hours and added dropwise to 500 mL of ice water with vigorous stirring. The resulting yellowish precipitate was collected and recrystallized from ethanol to give 2.6 g of the product as a faintly yellowish white solid, mp 261.5°–262.5° C.

Anal. Calcd for C$_{20}$H$_{20}$N$_2$O$_4$: C, 68.17; H, 5.72; N, 7.95. Found: C, 67.87; H, 5.73; N, 7.92. 67.93 5.79 7.84.

By using the procedures described in Examples 1–4, the following compounds in Table I were prepared or can be prepared.

TABLE I

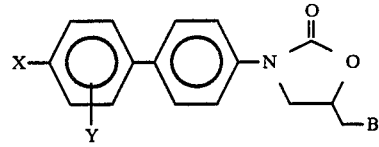

| Ex. | X | Y | B | Isomer | m.p. (°C.) |
|---|---|---|---|---|---|
| 1 | H | H | N$_3$ | l | 163.5–164.5 |
| 2 | H | H | NH$_2$ | l | 140–141 |
| 3 | H | H | NHCOCH$_3$ | l | 226–227 |
| 4 | 4'-CH$_3$CO$_3$ | H | NHCOCH$_3$ | l | 261.5–262.5 |
| 5 | 4'-CH$_3$CO$_3$ | H | NHCO$_2$CH$_3$ | l | |
| 6 | 4'-CH$_3$CO$_3$ | H | NHSO$_2$CH$_2$Cl | l | |
| 7 | 4'-CH$_3$CH$_2$CO | H | NHCOCH$_3$ | l | 253 |
| 8 | 4'-ClCH$_2$CO | H | NHCOCH$_3$ | l | 225 |
| 9 | 4'-HO$_2$C(CH$_2$)$_2$CO | H | NHCOCH$_3$ | l | 240–241 |
| 10 | 4'-HO$_2$CC(CH$_3$)$_2$CH$_2$CO | H | NHCOCH$_3$ | l | 222 (dec) |
| 11 | n-C$_3$H$_7$ | H | —NH$_2$ | l | |
| 12 | n-C$_3$H$_7$ | H | —NHCOCH$_3$ | l | |
| 13 | n-C$_5$H$_{11}$ | H | —NHCOCH$_3$ | l | |
| 14 | C$_2$H$_5$ | 3'-CH$_3$ | —N$_3$ | l | |
| 15 | C$_2$H$_5$ | 3'-CH$_3$ | —NHCOCH$_3$ | l | |
| 16 | H | 3'-Cl | —NHCOCH$_3$ | l | |
| 17 | Cl | 3'-CH$_3$ | —NHCOCH$_3$ | l | |
| 18 | C$_2$H$_5$ | 3'-F | —NHCOCH$_3$ | l | |
| 19 | CH$_3$ | 3'-F | —NHCOCH$_3$ | l | |

EXAMPLE 20

Preparation of
(l)-N-[3-(4-(4'-Iodophenyl)phenyl)-2-oxooxazolidin-5-ylmethyl]acetamide (I, Ar=4'—IC$_6$H$_4$, B=NHCOCH$_3$)

(l)-N-[3-(4-Phenylphenyl)-2-oxooxazolidin-5-ylmethyl]acetamide (20 g, 0.064 mole) in a mixture of trifluoroacetic acid (170 mL) and acetic acid (570 mL) was stirred and heated at 60° C. while adding dropwise a solution of iodine monochloride (139.2 g, 0.86 mole) in acetic acid (225 mL) during 6–7 hours. The mixture was stirred at 60° C. overnight, cooled to room temperature and filtered. The resulting filter cake was washed with ether (to remove excess iodine) and dried to give the desired iodo compound as a tan solid (20.8 g, 74%) which was 94% pure by HPLC. The filtrate was diluted with water and filtered to separate additional product 3.4 g. The main fraction was dissolved in dimethylformamide (200 mL) and filtered through a shallow bed of Darco ® or Celite ® (which one?). The filtrate was diluted with water (30 mL) and cooled to give pure product (9.1 g), mp 265°–267° C.

EXAMPLE 21

Preparation of
(l)-N-[3-(4-(4'-Formylphenyl)phenyl)-2-oxooxazolidin-5-ylmethyl]acetamide (I, Ar=4'—HCOC$_6$H$_4$, B=NHCOCH$_3$)

(l)-N-[3-(4-(4'-Iodophenyl)phenyl)-2-oxooxazolidin-5-ylmethyl]acetamide (4.41 g, 0.01 mole) was refluxed in dry tetrahydrofuran (500 mL) and flushed thoroughly with gaseous CO. Tetrakis(triphenyl-phosphine)palladium(O) (2.35 g, 0.002 mole) was added and the mixture stirred and heated at 50° C. under slight positive pressure of CO (balloon) while adding tributyltinhydride (2.94 g, 0.01 mole) in dry toluene (50 mL) during 6 hours. Heating and stirring under gaseous CO pressure was continued overnight. The reaction mixture was cooled to room temperature, added to petroleum ether (600 mL) and filtered to separate the desired aldehyde (3.33 g, 97%). Recrystallization from acetonitrile gave pure aldehyde product as fibrous white needles, mp 210° C.

The aldehyde can be readily converted to the corresponding carboxylic acid by oxidation with chromic acid in acetic acid.

EXAMPLE 22

Preparation of
(l)-N-[3-(4-(4'-(1-Hydroxyiminoethyl)phenyl)phenyl)-2-oxooxazolidin-5-ylmethyl]acetamide (I, Ar=4'—CH$_3$C(=NOH)C$_6$H$_4$, B=NHCOCH$_3$)

A mixture of 2.8 g of (l)-N-[3-(4-(4'-acetylphenyl)-phenyl)-2-oxooxazolidin-5-ylmethyl]acetamide, 5.6 g of hydroxylamine hydrochloride and 11.2 mL of pyridine in 560 mL of absolute ethanol was heated under reflux for 3 hours and the mixture was allowed to cool to room temperature. The solid formed was collected and washed with ethanol to give 2.58 g of the desired crude oxime, mp 268°–272° C. It can be further purified by recrystallization from ethanol.

EXAMPLE 23

Preparation of Sodium Salt of Succinate Hemiester of (l)-N-[3-(4-(4'-(1-Hydroxyiminoethyl)phenyl)phenyl)-2-oxooxazolidin-5-ylmethyl]acetamide (I, Ar=4'—CH$_3$C(=NOCOCH$_2$CH$_2$CO$_2$Na)C$_6$H$_4$, B=NHCOCH$_3$)

To a suspension of 1 g (2.72 mmol) of (l)-N-[3-(4-(4'-(1-hydroxyiminoethyl)phenyl)phenyl)-2-oxooxazolidin-5-ylmethyl]acetamide in 30 mL of DMF was added 135 mg (2.8 mmol) of NaH (50% dispersion in mineral oil) and the mixture was heated slowly to 40° C. when it became clear momentarily, then a massive precipitate formed as it was heated to 50° C. for 1 hour. The mixture was allowed to cool to 40° C., and 0.272 g (2.72 mmol) of succinic anhydride dissolved in a minimum volume of DMF was added. The thick white precipitate became opaque and easier to stir. It was heated at 50° C. for 0.5 hour, cooled to room temperature, and the precipitate was filtered and washed successively with DMF, glyme and ether to give 1.05 g of the sodium salt as a colorless white solid, mp 297°–300° (dec).

EXAMPLE 24

Preparation of
(l)-N-[3-(4-(4'-(1-Carboxymethoxyliminoethyl)phenyl)-phenyl)-2-oxooxazolidin-5-ylmethyl]acetamide (I, Ar=4'—CH$_3$C(=NOCH$_2$CO$_2$H)C$_6$H$_4$, B=NHCOCH$_3$)

A mixture containing 1 g of (l)-N-[3-(4-(4'-acetyl-phenyl)phenyl)-2-oxooxazolidin-5-ylmethyl]acetamide, 2 g of carboxymethoxyamine hydrochloride and 4 mL of pyridine in 180 mL of absolute ethanol was heated under reflux for 3 hours. The mixture was allowed to cool and white precipitate formed was collected and washed with ethanol to give 0.8 g of the desired product, mp 232° C. (dec). The sodium salt of the acid can be prepared by treating with aqueous sodium hydroxide and removing the water.

EXAMPLE 25

Preparation of
(l)-N-[3-(4-(4'-Acetylphenyl)phenyl)-2-oxooxazolidin-5-ylmethyl]acetamide 4-Methylpiperazinylhydrazone (I, Ar=4'—CH$_3$C(=NN(CH$_2$CH$_2$)$_2$NCH$_3$)C$_6$H$_4$, B=NHCOCH$_3$)

(l)-N-[3-(4-(4'-Acetylphenyl)phenyl)-2-oxooxazolidin-5-ylmethyl]acetamide (2.5 g, 0.0071 mole) and 1-amino-4-methylpiperazine (2.04 g, 0.018 mole) were heated at reflux in dry dioxane (350 mL) with borontrifluoride etherate (0.30 mL) overnight. The solvent was removed on a rotary evaporator and the product dried (80° C./0.1 mm) to give the titled hydrazine (3.19 g, 100%), mp 200° C. (dec).

EXAMPLE 26

Preparation of
(l)-N-[3-(4-(4'-(1-(4-Methylpiperazinylamino)ethyl))-phenyl-2-oxooxazolidin-5-ylmethyl]acetamide (I, Ar=4'—CH$_3$CH(NHN(CH$_2$CH$_2$)$_2$NCH$_3$)C$_6$H$_4$, B=NHCOCH$_3$)

(l)-N-[3-(4-(4'-Acetylphenyl)phenyl)-2-oxooxazolidin-5-ylmethyl]acetamide 4-Methylpiperazinylhydrazone (3.57 g, 0.0079 mole) was heated in methanol (250 mL) at reflux and then cooled to room temperature. A solution of NaBH$_3$CN (0.5 g, 0.0079 mole) and ZnCl$_2$ (0.5 g, 0.004 mole) in methanol (20 mL) was added and the mixture stirred at room temperature overnight followed by reflux for 0.5 hour. The reaction mixture was added to saturated Na$_2$CO$_3$ (75 mL) and water (200 mL) and extracted with CH$_2$Cl$_2$/MeOH (9/1, 5×100 mL). The extract was dried (MgSO$_4$) and the solvent removed on a rotary evaporator to give the product (2.91 g, 82%). The product was dissolved in 1N HCl (10 mL) and water (200 mL) and filtered to separate a solid (0.24 g). The clear filtrate was divided into two equal parts. One part was made basic with sodium carbonate and extracted with CH$_2$Cl$_2$/CH$_3$OH (9/1, 3×100 mL), dried and the solvent removed to give pure product (1.26 g), mp 120° C. The second portion was freeze dried to give the hydrochloride salt of the product (1.2 g), mp 168° C. (dec).

EXAMPLE 27

Preparation of
(l)-N-[3-(4-(4'-(1-Hydroxyethyl)phenyl)phenyl)-2-oxooxazolidin-5-ylmethyl]acetamide (I, Ar=4'—CH$_3$CH(OH)C$_6$H$_4$, B=NHCOCH$_3$)

To a suspension of 0.39 g of (l)-N-[3-(4-(4'-Acetylphenyl)phenyl)-2-oxooxazolidin-5-ylmethyl]acetamide in 100 mL of 95% ethanol was added 0.2 g of NaBH$_4$. The mixture was slowly heated to its boiling point when the mixture became homogeneous. Heating was continued for 15 minutes, diluted with 100 mL of water, brought it back to boiling, allowed to cool to room temperature and stripped to dryness. The resulting solid was triturated with water to give 0.36 g of white solid, mp 203.5°–208.5° C. It was recrystallized once from ethanol to give 0.26 g of the desired alcohol as white solid, mp 207.5°–212.5° C.

Anal. Calcd for C$_{20}$H$_{22}$N$_2$O$_4$: 354.1577 (M+) Observed m/e by HRMS: 354.1567.

By using the procedures described in Examples 20–27, the following compounds in Table II were prepared or can be prepared.

| | Anal calcd | C,68.05; | H,5.11; | N,12.53 |
|---|---|---|---|---|
| | Found | C,68.14; | H,5.14; | N,12.40 |
| | | 68.05 | 5.06 | 12.49 |

HRMS m/e calcd: 335.1270, measured 335.1268.

EXAMPLE 38

Preparation of
(l)-N-[3-(4-(4'-(5-Tetrazolyl)phenyl)phenyl)-2-oxooxazolidin-5-ylmethyl]acetamide (I, Ar=4'—N$_4$CC$_6$H$_4$, B=NHCOCH$_3$ (l)-N-[3-(4-(4'-Cyanophenyl)phenyl)-2-oxooxazolidin-5-ylmethyl]acetamide (2.68 g, 0.0080 mole) was heated in dimethylformamide (25 mL) with trimethylsilyl azide (1.89 g, 0.016 mole) at 140° C. for 5.5 hours. More azide (1.8 g, 0.016 mole) was added and heating at 140° C. was continued for a total of 45 hours. The reaction mixture was poured onto ice and centrifuged to separate a brown solid which was washed with water and dried (2.71 g, 90%). The product was purified by chromatography on silica and eluted with

TABLE II

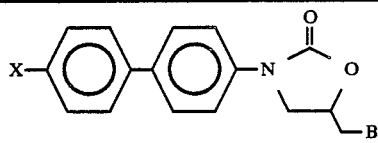

| Ex. | X | B | Isomer | m.p. (°C.) |
|---|---|---|---|---|
| 20 | 4'-I | NHCOCH$_3$ | 1 | 265–267 |
| 21 | 4'-HCO | NHCOCH$_3$ | 1 | 210 |
| 22 | 4'-CH$_3$C(=NOH) | NHCOCH$_3$ | 1 | 268–272 |
| 23 | 4'-CH$_3$C(=NOCOCH$_2$CH$_2$CO$_2$Na) | NHCOCH$_3$ | 1 | 297–300 (dec) |
| 24 | 4'-CH$_3$C(=NOCH$_2$CO$_2$H) | NHCOCH$_3$ | 1 | 232 (dec) |
| 25 | 4'-CH$_3$C(=NN(CH$_2$CH$_2$)$_2$NCH$_3$) | NHCOCH$_3$ | 1 | 200 (dec) |
| 26 | 4'-CH$_3$CH(NHN(CH$_2$CH$_2$)$_2$NCH$_3$) | NHCOCH$_3$ | 1 | 168 (dec) |
| 27 | 4'-CH$_3$CH(OH) | NHCOCH$_3$ | 1 | 207.5–212.5 |
| 28 | 4'-HOCH$_2$ | NHCOCH$_3$ | 1 | 235 |
| 29 | 4'-CH$_3$CH(OCOCH$_2$CH$_2$CO$_2$H) | NHCOCH$_3$ | 1 | 156 |
| 30 | 4'-CH$_3$CH(OCOCH$_2$CH$_2$CO$_2$Na) | NHCOCH$_3$ | 1 | |
| 31 | 4'-CH(=NOH) | NHCOCH$_3$ | 1 | |
| 32 | 4'-CH(=NOCH$_2$CO$_2$H) | NHCOCH$_3$ | 1 | |
| 33 | 4'-CH(=NN(CH$_2$CH$_2$)$_2$NCH$_3$) | NHCOCH$_3$ | 1 | |
| 34 | 4'-CH$_3$CH$_2$C(=NOH) | NHCOCH$_3$ | 1 | |
| 35 | 4'-CH$_3$CH$_2$C(=NOCOCH$_2$CH$_2$CO$_2$H) | NHCOCH$_3$ | 1 | |
| 36 | 4'-CH$_3$CH$_2$CH(OH) | NHCOCH$_3$ | 1 | |

EXAMPLE 37

Preparation of
(l)-N-[3-(4-(4'-Cyanophenyl)phenyl)-2-oxooxazolidin-5-ylmethyl]acetamide (I, Ar=4'—NCC$_6$H$_4$, B=NHCOCH$_3$)

(l)-N-[3-(4-(4'-Iodophenyl)phenyl)-2-oxooxazolidin-5-ylmethyl]acetamide (20.10 g, 0.046 mole) and cuprous cyanide (16.0 g, 0.16 mole) in N-methylpyrrolidinone (270 mL) were stirred and heated at 125° C. for 24 hours. The reaction mixture was cooled to room temperature, poured into ice water, and filtered to separate a brown solid. The solid was added to a column packed with silica (84 g) and eluted with CHCl$_3$/CH$_3$OH (9/1, 1000 mL) and methanol (750 mL). The combined eluents were evaporated to dryness on a rotary evaporator to give the product (12.6 g, 81%) which was 96% pure by HPLC. This material was recrystallized from chloroform to give the pure cyano compound, mp 208°–209° C.

CHCl$_3$/CH$_3$OH (9/1) and then with methanol. The methanol fraction proved to be the pure product, mp 244° C. (dec). The sodium salt of the product can be prepared by treating with aqueous sodium hydroxide and removing the water.

EXAMPLE 39

Preparation of
(l)-N-[3-(4-(4'-((N,N-Methylethylamino)methyl)-phenyl)phenyl)-2-oxooxazolidin-5-ylmethyl]acetamide (I, Ar=4'—CH$_3$CH$_2$N(CH$_3$)CH$_2$C$_6$H$_4$, B=NHCOCH$_3$)

(l)-N-[3-(4-(4'-Formylphenyl)phenyl)-2-oxooxazolidin-5-ylmethyl]acetamide (1.7 g, 0.005 mole) and ethylmethylamine (1.48 g, 0.025 mol) were heated at reflux in methanol (170 mL). The mixture was cooled to 25° C. and a solution of sodium cyanoborohydride (0.315 g, 0.005 mole) in methanol (12.1 mL) was added and the mixture stirred at room temperature overnight. The reaction mixture was added to saturated sodium bicarbonate (25 mL) and water (100 mL) and extracted with CH₂Cl₂/MeOH (9/1, 3×100 mL). The extract was dried (MgSO₄), filtered and the solvent removed on a rotary evaporator to give a white solid which was triturated with ether and dried to give the product (1.65 g, 86%). The product was dissolved in 1N HCl (10 mL) and water (150 mL) to give a clear solution. One half of this solution was made basic with sodium carbonate and extracted with CH₂Cl₂/CH₃OH (9/1, 3×100 mL). The extract was dried (MgSO₄), filtered and the solvent removed to give pure amine (0.84 g), mp 162°–164° C. The residual acidic solution was freeze dried to give the hydrochloride salt of the amine (0.32 g), mp 145°–147° C. (dec).

With primary amines, the reaction may stop at the imine stage when the reduction is carried out at room temperature. Refluxing the reaction mixture for 1–3 hours with a small excess of NaBH₃CN or NaBH₄ completes the reduction.

Reductive alkylation of ketones frequently fails with NaBH₃CN/ZnCl₂ but the intermediate hydrazone can be prepared and reduced as described previously in Example 27.

By using the procedures described in Examples 37–39, the following compounds in Table III were prepared.

EXAMPLE 57

Preparation of (l)-N-[3-(4-(4'-(3-N,N-dimethylaminopropionyl)-phenyl)phenyl)-2-oxooxazolidin-5-ylmethyl]acetamide (I, Ar=4'—(CH₃)₂NCH₂CH₂COC₆H₄, B=NHCOCH₃)

N,N,N',N'-Tetramethyldiaminomethane (0.29 g, 0.0028 mole) was added dropwise to trifluoroacetic acid (5 mL) cooled at −10° C. and stirred for 10 minutes. (l)-N-[3-(4-(4'-Acetylphenyl)phenyl)-2-oxooxazolidin-5-ylmethyl]acetamide (1.0 g, 0.0028 mol) was added slowly as a solid at −10° C. The cooling bath was removed and the mixture stirred while warming slowly to room temperature. The reaction temperature was then gradually raised to 60°–65° C. and heated at this temperature overnight. The reaction mixture was added dropwise to saturated sodium carbonate (50 mL) cooled in an ice bath. The resulting mixture was filtered and the yellow solid washed with water and dried to give the product, 1.12 g, 97%, mp 192°–194° C.

A portion of the product (0.5 g) was dissolved in 1N HCl (10 mL) and water (50 mL), filtered and the clear yellow solution freeze dried to give hydrochloride salt of the ketoamine (0.4 g), mp 150° C. gassing, 195° C. (dec).

When the Mannich resection was carried out using bis-(N-methylpiperidinyl)methane and propionyl derivative (I, Ar=4'—CH₃CH₂COC₆H₄—,

TABLE III

| Ex. | X | B | Isomer | m.p. (°C.) |
|---|---|---|---|---|
| 37 | 4'-NC | NHCOCH₃ | l | 208–209 |
| 38 | 4'-N₄C | NHCOCH₃ | l | 244 (dec) |
| 39 | 4'-CH₃CH₂N(CH₃)CH₂ | NHCOCH₃ | l | 162–164 |
| 40 | 4'-CH₃NHCH₂ | NHCOCH₃ | l | 197 (dec) |
| 41 | 4'-(CH₃)₂NCH₂ | NHCOCH₃ | l | 197 |
| 42 | 4'-CH₃CH₂NHCH₂ | NHCOCH₃ | l | 180 |
| 43 | 4'-(CH₃CH₂)₂NCH₂ | NHCOCH₃ | l | 137 (dec) |
| 44 | 4'-(n-Pr)₂NCH₂ | NHCOCH₃ | l | 128 |
| 45 | 4'-(n-C₄H₉NHCH₂ | NHCOCH₃ | l | 200 |
| 46 | 4'-(n-C₄H₉)₂NCH₂ | NHCOCH₃ | l | 107 |
| 47 | 4'-(n-C₅H₁₁)₂NCH₂ | NHCOCH₃ | l | 142 |
| 48 | 4'-n-C₈H₁₇N=CH | NHCOCH₃ | l | 210 |
| 49 | 4'-n-C₈H₁₇NHCH₂ | NHCOCH₃ | l | 209 |
| 50 | 4'-(HOCH₂CH₂)₂NCH₂ | NHCOCH₃ | l | 123 |
| 51 | 4'-CH₃N(CH₂CH₂)₂NNHCH₂ | NHCOCH₃ | l | 194 (dec) |
| 52 | 4'-CH₃COCH—NCH₂·HCl (piperidine ring) | NHCOCH₃ | l | 100 |
| 53 | 4'-O morpholino NCH₂ | NHCOCH₃ | l | |
| 54 | 4'-CH₃OCH₂CH₂CH₂NHCH₂ | NHCOCH₃ | l | |
| 55 | 4'-(CH₃)₂NCH₂CH₂NHCH₂ | NHCOCH₃ | l | |
| 56 | 4'-CH₃N piperazinyl NCH₂ | NHCOCH₃ | l | |

B=NHCOCH₃), an elimination product (I, Ar=4'—CH₂=C(CH₃)COC₆H₄—, B=NHCOCH₃) was also obtained (Example 63).

EXAMPLE 58

Preparation of
(l)-N-[3-(4-(4'-(3-N,N-Dimethylamino-1-hydroxypropyl)phenyl)phenyl)-2-oxooxazolidin-5-ylmethyl]acetamide (I,
Ar=4'—(CH₃)₂NCH₂CH₂CH(OH)C₆H₄, B=NHCOCH₃)

(l)-N-[3-(4-(4'-3-N,N-Dimethylaminopropionyl)phenyl)phenyl)-2-oxooxazolidin-5-ylmethyl]acetamide (3.14 g, 0.0077 mole) in acetic acid (35 mL) was stirred with NaBH₃CN (1.93 g) at room temperature overnight. The solution was added dropwise to saturated sodium carbonate (400 mL) and the pH adjusted to 9-10. The mixture was extracted with CH₂Cl₂/CH₃OH, (9/1, 4×150 mL). The extract was dried and the solvent removed to give the crude reduced amine (2.74 g, 87%). The compound was chromatographed on silica gel by eluting with CHCl₃/CH₃OH (9/1) to give pure amine, mp 194° C. A portion of the amine was dissolved in dilute HCl and freeze dried to give the hydrochloride salt.

By using the procedures described in Examples 57 and 58, the following compounds in Table IV were prepared or can be prepared.

was added to 56.8 mL (0.246 mol) of triisopropylborate in tetrahydrofuran at −70° C. The borate ester was hydrolyzed with 10% sodium hydroxide solution, then acidified to give the boronic acid. Recrystallization from water gave 11.0 g of the boronic acid, mp 162°-163° C.

A mixture of 2.5 g (0.015 mol) of the above boronic acid in 40 mL of DMF, 4.2 mL of triethylamine, 3.6 g of (l)-N-[3-(4-iodophenyl)-2-oxooxazolidin-5-ylmethyl]acetamide, 0.2 g of tri-2-tolylphosphine and 80 mg of palladium acetate was subjected to four "Firestone" cycles. The homogeneous solution was held at 100° C. under nitrogen for 72 hours, cooled, and filtered. The DMF was removed at 70° C. (0.5 mm Hg) and the residue dissolved in methylene chloride and washed with 10% ammonium hydroxide solution, dried over magnesium sulfate and solvent evaporated to give 2.31 g of crude material which was chromatographed on 70 g of silica gel with an eluent of methylene chloride-acetone to give 1.24 g of material consistent with product. Recrystallization from acetonitrile gave 0.8 g of pure (l)-N-[3-(4-(3'-methylthiophenyl)phenyl)-2-oxooxazolidin-5-ylmethyl]acetamide.

A mixture of 0.51 g (0.0014 mol) of the sulfide in 155 mL of chloroform was held at reflux to dissolve the solid, then cooled to −30° C., and a solution of 0.30 g (0.0014 mol) of 82% m-chloroperbenzoic acid in 15 mL of methylene chloride was added at −30° C., then al-

TABLE IV

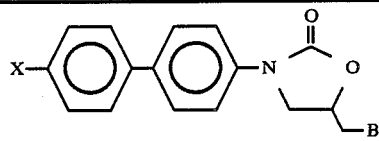

| Ex. | X | B | Isomer | m.p. (°C.) |
|---|---|---|---|---|
| 57 | 4'-(CH₃)₂NCH₂CH₂CO | NHCOCH₃ | l | 192-194 |
| 58 | 4'-(CH₃)₂NCH₂CH₂CH(OH) | NHCOCH₃ | l | 194 |
| 59 | 4'-O(CH₂CH₂)₂NCH₂CH₂CH(OH) | NHCOCH₃ | l | 165 |
| 60 | 4'-CH₃N(CH₂CH₂)₂NCH₂CH₂CO | NHCOCH₃ | l | 221 |
| 61 | 4'-CH₃N(CH₂CH₂)₂NCH₂CH₂CH(OH) | NHCOCH₃ | l | 151 (dec) |
| 62 | 4'-CH₃N(CH₂CH₂)₂NCH₂CH(CH₃)CO | NHCOCH₃ | l | 105 |
| 63 | 4'-CH₂=C(CH₃)CO | NHCOCH₃ | l | 216 |
| 64 | 4'-CH₃N(CH₂CH₂)₂NCH₂CH(CH₃)CH(OH) | NHCOCH₃ | l | 180 |

EXAMPLE 65

Preparation of
(l)-N-[3-(4-(3'-Methylsulfenylphenyl)phenyl)-2-oxooxazolidin-5-ylmethyl]acetamide (I, Ar=3'—CH₃SOC₆H₄, B=NHCOCH₃)

To a mixture containing 23.4 g (0.1 mol) of (l)-N-(3-phenyl-2-oxooxazolidin-5-ylmethyl)acetamide and 29 g (0.13 mol) of silver trifluoroacetate, 300 mL of acetonitrile and 200 mL of chloroform was added 27 g of iodine in one portion and allowed to stir at room temperature overnight. The mixture was filtered and the filtrate was concentrated under reduced pressure to give a brown solid which was triturated with distilled water, filtered and washed thoroughly with distilled water. The resulting solid was recrystallized from 200 mL of acetonitrile (activated charcoal used) to give 27.5 g (77%) of (l)-N-[3-(4-iodophenyl)-2-oxooxazolidin-5-ylmethyl]acetamide (XXIV) as a colorless crystalline solid, m.p. 194.5°-195.5° C.

A Grignard reagent was prepared from 25 g (0.123 mol) of m-bromothioanisole and 3.59 g (0.148 mol) of magnesium in 125 mL of tetrahydrofuran. This solution lowed to warm to −20° C. After addition of 0.1 mL of dimethylsulfide, the mixture was warmed to 20° C. and the solvent removed. The residue was dissolved in chloroform and washed with saturated sodium bicarbonate solution, dried over potassium carbonate and solvent evaporated. The residue was chromatographed on 25 g of silica gel with methylene chloride-acetone as the eluent. The product was dissolved in water, filtered (0.2 micron membrane filter) and the water removed. The residue was recrystallized from isopropanol to give 180 mg of the sulfoxide, mp 162°-167° C. ¹H-NMR (d₆-DMSO) δ 8.27 (m, 1H), 7.93 (s, 1H), 7.80 (m, 3H), 7.67 (m, 4H), 4.73 (m, 1H), 4.20 (t, 1H), 3.80 (t, 1H), 3.45 (m, 2H), 2.80 (s, 3H), 1.83 (s, 3H); IR (KBr): 3280, 1750; 1665, 1610, 1520, 1050 cm⁻¹.

The sulfoxide can further oxidize to sulfone by reacting with excess MCPBA in chloroform under reflux for 3 hours.

EXAMPLE 66

Preparation of
(l)-N-[3-(4-(4'-N,N-Dimethylaminoethyloxyphenyl)-phenyl)-2-oxooxazolidin-5-ylmethyl]acetamide (I, Ar=4'—(CH₃)₂NCH₂CH₂OC₆H₄, B=NHCOCH₃)

A freshly prepared solution of 4-benzyloxyphenyl magnesium bromide (from 21.05 g of 4-benzyloxybromobenzene and 2.2 g of magnesium metal) in tetrahydrofuran (80 mL) was added carefully to a stirred solution of freshly fused zinc chloride (17.14 g) in tetrahydrofuran maintained at 0°-5° C. The resulting mixture was stirred at room temperature for 30 minutes and then treated with (l)-N-[3-(4-iodophenyl)-2-oxooxazolidin-5-yl]methylacetamide (14.4 g), added in one lot, followed by the addition of bis(triphenylphosphine)nickel(II) chloride (4.0 g). The mixture was stirred at room temperature for 90 minutes and then poured into an excess of ice and 1N HCl and the solid that separated filtered off, washed with water, boiled with tetrahydrofuran and filtered. The solid was washed with a small quantity of tetrahydrofuran followed by hexanes and air-dried to yield 9.72 g of (l)-N-[3-(4-(4'-benzyloxyphenyl)phenyl)-2-oxooxazolidin-5-ylmethyl]acetamide as a colorless solid, mp 235°-237° C. (dec). It was pure enough to be used in the next step. An analytical sample was prepared by recrystallizing a small quantity of the product from acetic acid, mp 243°-245° C. (dec).

A suspension of the benzyloxy compound (6.74 g) in a solution of hydrogen bromide in acetic acid (72 mL; 30.32%) was stirred and heated under reflux for 10 to 15 minutes, cooled and filtered. The colorless solid was washed with ether and air-dried to yield (l)-N-[3-(4-(4'-hydroxyphenyl)phenyl)-2-oxooxazolidin-5-ylmethyl]acetamide (4.03 g), mp 280°-281° C. (dec).

Sodium hydride (0.5 g; 50% oil dispersion) was added in small portions to a stirred solution of the phenolic compound (3.26 g) in warm dimethylformamide (75 mL) and, after the addition was complete, the mixture was stirred at room temperature for 15 minutes and then treated with a freshly prepared solution of 2-dimethylaminoethyl chloride (from 6.0 g of the hydrochloride and aq NaHCO₃) in benzene (30 mL) added in one lot. The resulting mixture was stirred and heated at 90°-100° C. overnight and then stripped of the solvents under reduced pressure. The residue was triturated with water and filtered. The solid was dissolved in requisite volume of methylene chloride and the solution extracted twice with 1N HCl (50 mL each time). The combined acid extracts were filtered to remove traces of undissolved material and the filtrate cooled and basified with conc. ammonium hydroxide. The mixture was extracted twice with methylene chloride and the combined methylene chloride extracts were washed with H₂O, dried over MgSO₄ and stripped of the solvent under reduced pressure to yield a solid which was recrystallized from isopropanol to furnish 1.4 g of (l)-N-[3-(4-(4'-N,N-Dimethylaminoethyloxyphenyl)phenyl)-2-oxooxazolidin-5-ylmethyl]acetamide as a colorless solid, mp 202°-204° C.

EXAMPLE 67

Preparation of
(l)-N-[3-(4-(4'-Methylthiophenyl)phenyl)-2-oxooxazolidin-5-ylmethyl]acetamide (I, Ar=4'—CH₃SC₆H₄—, B=NHCOCH₃)

A Grignard reagent was prepared from 12.2 g (0.06 mol) of p-bromothioanisole and 1.7 g (0.07 mol) of magnesium in 70 mL of tetrahydrofuran. This solution was added to 22.7 mL of triisopropylborate in tetrahydrofuran at −70° C. The borate ester was hydrolyzed with 150 mL of 1N sodium hydroxide solution and most of the tetrahydrofuran from the mixture was removed under reduced pressure. Acidification of the basic solution with 10% hydrochloric acid gave 9.28 g of the crude boronic acid. Recrystallization from water gave 3.8 g of pure p-methylmercaptophenylboronic acid as a colorless, crystalline solid, m.p. 211.5°-212° C.

A mixture of 2.52 g (0.015 mol) of the above boronic acid in 40 mL of DMF, 4.2 mL of triethylamine, 3.6 g of (l)-N-[3-(4-iodophenyl)-2-oxooxazolidin-5-ylmethyl]acetamide, 0.2 g of tri-2-tolylphosphine and 80 mg of palladium acetate under nitrogen atmosphere was heated at 100° C. for 72 hrs., cooled, and diluted with 40 mL of ether. The solid precipitate formed was filtered, washed successively with ether, water, sodium bicarbonate and water to give a crude product. The crude product was recrystallized once from ethanol to give 1.3 g of pure (l)-N-[3-(4-(4'-methylthiophenyl)phenyl)-2-oxooxazolidin-5-ylmethyl]acetamide, m.p. 244.5°-246.5° C. HRMS: Calcd. 356.1195; Measured, 356.1168.

EXAMPLE 68

Preparation of
(l)-N-[3-(4-(4'-Methylsulfenylphenyl)phenyl)-2-oxooxazolidin-5-ylmethyl]acetamide (I, Ar=4'—CH₃SOC₆H₄—, B=NHCOCH₃)

A mixture of 0.6 g (1.68 mmol) of the sulfide of Example 67 in 250 mL of chloroform was heated to dissolve the solid, then cooled to −30° C., and 0.36 (1.68 mmol) of 82% m-chloroperbenzoic acid was added at −30° C., then allowed to slowly warm to −10°. Trace of insoluble material was removed by filtration and the filtrate was diluted with ether to precipitate 0.59 g of the sulfoxide, m.p. 217°-219° C. The product was shown to be at least 99% pure by hplc. An nmr (CDCl₃) showed absence of any sulfone resonance. HRMS: Calcd. 372.1144; Measured, 372.1156.

EXAMPLE 69

Preparation of
(l)-N-[3-(4-(4'-Methylsulfonylphenyl)phenyl)-2-oxooxazolidin-5-ylmethyl]acetamide (I, Ar=4'—CH₃SO₂C₆H₄—, B=NHCOCH₃)

A mixture of 0.4 g (1.1 mmol) of the sulfide of Example 67 and 0.53 g (2.45 mmol) of 82% m-chloroperbenzoic acid in 200 mL of chloroform was heated under reflux for 2.5 h. The mixture was cooled and diluted with ether to precipitate the desired sulfone, 0.4 g, m.p. 259°-260.5° C. dec. The product was shown to be homogeneous by hplc. HRMS: Calcd. 338.1089; Measured, 338.1126.

By using the procedures described in Examples 65-69, the following compounds in Table V were prepared or can be prepared.

TABLE V

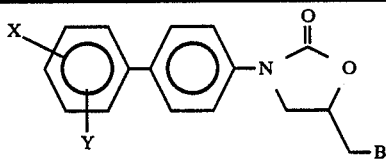

| Ex. | X | Y | B | Isomer | m.p.(°C.) |
|---|---|---|---|---|---|
| 65 | 3'-CH$_3$SO | H | NHCOCH$_3$ | l | 162–167 |
| 66 | 4'-(CH$_3$)$_2$NCH$_2$CH$_2$O | H | NHCOCH$_3$ | l | 202–204 |
| 67 | 4'-CH$_3$S | H | NHCOCH$_3$ | l | 244.5–246.5 |
| 68 | 4'-CH$_3$SO | H | NHCOCH$_3$ | l | 217–219 |
| 69 | 4'-CH$_3$SO$_2$ | H | NHCOCH$_3$ | l | 259–260.5 (dec) |
| 70 | 3'-CH$_3$CH$_2$ | H | NHCOCH$_3$ | l | 121–122 |
| 71 | 2'-CH$_3$ | H | NHCOCH$_3$ | l | 181–183 |
| 72 | 3'-HCO | H | NHCOCH$_3$ | l | 146–147 |
| 73 | 3'-NH$_2$ | H | NHCOCH$_3$ | l | 220–221 |
| 74 | 3'-(CH$_3$)$_2$N | H | NHCOCH$_3$ | l | 163–163.5 |
| 75 | 4'-CH$_3$O | H | NHCOCH$_3$ | l | 239–241 (dec) |
| 76 | 4'-(CH$_3$)$_2$N(CH$_2$)$_3$O | H | NHCOCH$_3$ | l | 191–193 |
| 77 | 4'-C$_6$H$_5$CH$_2$OCOCH$_2$O | H | NHCOCH$_3$ | l | 186–187 |
| 78 | 4'-HO$_2$CCH$_2$O | H | NHCOCH$_3$ | l | 228–230 (dec) |
| 79 | 4'-F | H | NHCOCH$_3$ | l | 229–230 (dec) |
| 80 | 4'-Cl | H | NHCOCH$_3$ | l | 249–250 (dec) |
| 81 | 4'-CH$_3$ | 5'-CH$_3$ | NHCOCH$_3$ | l | 168–169 |
| 82 | 3'-CH$_3$ | 5'-CH$_3$ | NHCOCH$_3$ | l | 106–107 |
| 83 | 4'-F | 5'-F | NHCOCH$_3$ | l | 201.5–203 |
| 84 | 3'-F | 5'-F | NHCOCH$_3$ | l | 204–204.5 |

EXAMPLE 85

Preparation of (l)-N-[3-(4-(4'-Pyridyl)phenyl)-2-oxooxazolidin-5-ylmethyl]acetamide (I, Ar=4'—NC$_5$H$_4$, B=NHCOCH$_3$ To a stirred solution of 75 g (0.386 mol) of 4-bromopyridine hydrochloride in 400 mL of ether and 200 mL of water (2 layer system) was added 40 g of sodium carbonate (0.38 mol) in several portions. The water was separated, the ether layer was washed once with brine, dried (MgSO$_4$) and most of the solvent was removed under reduced pressure. As soon as the vacuum started to improve indicating that most of the ether was removed, 200 mL of fresh anhydrous ether was added and the solvent was again removed. This process was repeated once more to minimize any moisture present. To the residue still containing small amount of ether was added 750 mL of ether immediately. The solution was cooled to −78° C., and 185 mL (0.462 mol, 20% excess) of 2.5N n-butyllithium (in hexane) was added at such a rate that the temperature of the reaction mixture remained below −65° C. (~20 min). When the temperature returned to below −70°, 92.2 g (0.463 mol) of trimethyltin chloride dissolved in 200 mL of ether was added at below −65° C. When the addition was complete, it was stirred at −75° C. for 0.5 hour, and then the cooling bath was removed to allow the temperature of the reaction to slowly rise. When the temperature of the reaction reached −20° C., 10 mL of methanol followed by 200 mL of water were added and the mixture was allowed to come to room temperature. The ether layer was washed once with brine, dried (MgSO$_4$) and the solvent was evaporated under reduced pressure to give 114 g of a light tan liquid. The pure product was isolated by distillation through a 30 cm Vigreux column, bp 40°–42° C. (0.1 mm), [bp 32°–34° C. (0.07 mm)]. n-Butyltrimethyltin, a by-product, distills at below room temperature at this pressure and separates well by distillation through the 30 cm Vigreux column.

A mixture containing 74.5 g (0.207 mol) of (l)-N-[3-(4-iodophenyl)-2-oxooxazolidin-5-ylmethyl]acetamide, 60 g (0.248 mol) of 4-pyridyltrimethyltin, 23 g (0.033 mol) of freshly prepared bis(triphenylphosphine)palladium-(II) chloride and 71 mL of triethylamine in 1300 mL of dry dimethyformamide (DMF) was heated at 50°–60° C. until all of the iodophenyloxazolidinone is used up (24–48 hours) as monitored by HPLC. The insoluble catalyst was removed by filtration through a bed of Celite ® and the volatile material and all of the solvent (DMF) from the filtrate was removed under reduced pressure (<40° C.). The resulting oil was taken up in 500 mL of chloroform and diluted with 1.5 L of ether to give a tan precipitate. The precipitate was filtered and dried under a stream of nitrogen, digested with 1 L of 1N HCl, filtered to remove insoluble material and neutralized to pH of 8 using conc. ammonium hydroxide at 10°–20° C. The off-white precipitate was collected on a filter, dissolved in 400 mL of hot 95% ethanol, treated with charcoal, and diluted with 700 mL of water. The solution was concentrated under reduced pressure to remove most of the ethanol to give an off-white precipitate. The precipitate was collected on a filter and washed with a small amount of ice water and dried to give 26 g (40.3% theory) of the product, mp 188°–190° C. Several other runs conducted under the same conditions gave products in 40–45% yields. The material can be further purified by recrystallization from absolute ethanol, or repeating the work-up procedure to give analytically pure sample of (l)-N-[3-(4-(4-pyridyl)-phenyl)-2-oxooxazolidin-5-ylmethyl]acetamide as a colorless white solid, mp 191°–192° C.

| Anal. Calcd for C$_{17}$H$_{17}$N$_3$O$_3$ | C, 65.58; | H, 5.50; | N, 13.50 |
|---|---|---|---|
| Found | C, 65.33; | H, 5.67; | N, 13.37 |
| | 65.35 | 5.53 | 13.38 |

Following a procedure similar to the one described in Example 65, amine oxide derivatives of the pyridyl compounds were prepared by treating with excess MCPBA.

1-N-[3-(4-Tri-n-butylstannylphenyl)-2-oxooxazolidin-5-yl-methyl]acetamide was prepared as follows.

To a mixture of 7.0 mL of hexabutylditin, 3.60 g of (l)-N-[3-(4-iodophenyl)-2-oxooxazolidin-5-ylmethyl]-acetamide and 25 mL of DMF under nitrogen, which had been subjected to several Firestone cycles to remove oxygen, was added 0.16 g of (PhCN)$_2$PdCl$_2$ with stirring and the mixture was stirred at 70° C. overnight. The mixture was poured into 500 mL of water and extracted with ethyl acetate, which was dried (MgSO$_4$), filtered through a Celite ® pad to remove both Pd and the MgSO$_4$, and evaporated in vacuo. The mixture was chromatographed on silica with chloroform to give the pure (l)-N-[3-(4-tri-n-butylstannylphenyl)-2-oxooxazolidin-5-ylmethyl]acetamide free from tributyltin iodide by-product as a contaminant. Isolated was 3.21 g.

By using the procedures described in Example 85, the following compounds in Table VI were prepared or can be prepared.

TABLE VI.

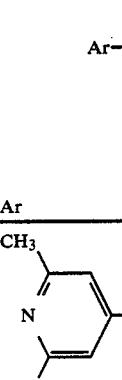

| Ex. | Ar | B | Isomer | m.p.(°C.) |
|---|---|---|---|---|
| 85 | 4'-NC$_5$H$_4$ | NHCOCH$_3$ | l | 191–192 |
| 86 | 2'-NC$_5$H$_4$ | NHCOCH$_3$ | l | 170–173 |
| 87 | 2'-ONC$_5$H$_4$ | NHCOCH$_3$ | l | 110 (dec) |
| 88 | 3'-NC$_5$H$_4$ | NHCOCH$_3$ | l | 183–185 |
| 89 | 3'-ONC$_5$H$_4$ | NHCOCH$_3$ | l | 220 (dec) |
| 90 | 4'-ONC$_4$H$_4$ | NHCOCH$_3$ | l | |
| 91 | 4'-ClC$_6$H$_4$ | NHCOCH$_3$ | l | 249–250 |
| 92 | 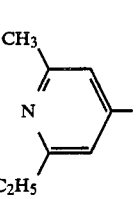 | NHCOCH$_3$ | l | 221–222 (dec) |
| 93 | 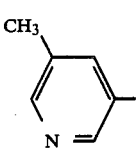 | NHCOCH$_3$ | l | 196 (dec) |
| 94 | 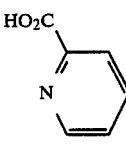 | NHCOCH$_3$ | l | |
| 95 | 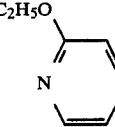 | NHCOCH$_3$ | dl | |

TABLE VI-continued

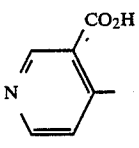

| Ex. | Ar | B | Isomer | m.p.(°C.) |
|---|---|---|---|---|
| 96 | 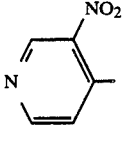 | NHCOCH$_3$ | dl | |
| 97 | 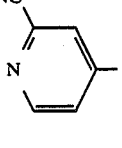 | NHCOCH$_2$Cl | l | |
| 98 | 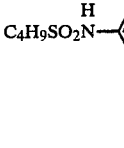 | NHSOCH$_3$ | l | |
| 99 |  | NHCOC$_3$H$_7$ | l | |
| 100 | | NHSO$_2$C$_2$H$_5$ | l | |
| 101 | | NHCOCH$_3$ | l | |
| 102 | | N$_3$ | l | |
| 103 | | NH$_2$ | l | |
| 104 | | NHCOCH$_3$ | l | |

TABLE VI-continued

Ar—⟨phenyl⟩—N(oxazolidinone-2-one)—B

| Ex. | Ar | B | Isomer | m.p.(°C.) |
|---|---|---|---|---|
| 105 | CH₃S—⟨pyridyl⟩— | NHCOCH₃ | l | |
| 106 | CH₃SO—⟨phenyl⟩— (S=O) | NHCOCH₃ | l | |
| 107 | C₃H₇NH—⟨pyridyl⟩— | NHCOCH₃ | l | |
| 108 | ⟨furyl (O)⟩ | NHCOCH₃ | l | |
| 109 | ⟨thienyl (S)⟩ | NHCOCH₃ | l | |
| 110 | ⟨N-methylpyrrolyl⟩ | NHCOCH₃ | l | |
| 111 | ⟨pyrimidinyl⟩ | NHCOCH₃ | l | |
| 112 | ⟨pyrazinyl⟩ | NHCOCH₃ | l | |

EXAMPLE 113

Preparation of (l)-N-[3-(4-(2',5'-Dihydroxyphenyl)phenyl)-2-oxooxazolidin-5-ylmethyl]acetamide (I, Ar=2',5'—(HO)₂C₆H₄, B=NHCOCH₃)

(l)-N-[3-(4-Nitrophenyl)-2-oxooxazolidin-5-ylmethyl]acetamide was prepared according to the procedures previously described in U.S. Pat. No. 4,705,799. The nitro compound was reduced to the corresponding amino derivative by catalytic hydrogenation in 95% ethanol in the presence of platinum oxide under 40 psig of hydrogen pressure.

To a mixture containing 1 g (4 mmol) of (l)-N-[3-(4-aminophenyl)-2-oxooxazolidin-5-ylmethyl]acetamide, 1 mL of 28% HCl and 4 g of ice was added a solution of 0.28 g of sodium nitrite in 1 mL of water dropwise at 0°–5° C. After the addition was complete, the mixture was tested with starch/iodide paper to insure the reaction was complete. The mixture after being made neutral (pH 6–7) by cautious addition of sodium carbonate dropwise to a solution of 0.65 g (50% excess) of benzoquinone dissolved in a minimum amount (~15 mL) of 95% ethanol with vigorous stirring at 10°–15° C. The mixture was allowed to come to room temperature, stirred for 1 hour and diluted with 200 mL of water. The desired benzoquinone attached phenyloxazolidinone was obtained as a brick colored solid, 0.95 g, mp 218°–219.5° C. It was recrystallized once from acetonitrile to give 0.4 g of the pure quinone derivative as a golden orange solid, mp 235°–236° C.

To the orange solid (1.6 g, 4.7 mmol) suspended in 45 mL of 95% ethanol was added 0.5 g of sodium borohydride. A slight exotherm was noted and the mixture became homogeneous in 10 minutes. Water (50 mL) was added and the mixture was warmed to 50° C. After allowing to cool, most of the ethanol was removed under reduced pressure and the resulting aqueous solution was made acidic (pH 1) with 6M HCl to precipitate the product. The product was obtained as a light grayish purple solid, 1.03 g, mp 227°–228.5° C.

EXAMPLE 114

Preparation of (l)-N-[3-(4-(4'-Ethylphenyl)phenyl)-2-oxooxazolidin-5-ylmethyl]acetamide (I, Ar=4'—CH₃CH₂C₆H₄, B=NHCOCH₃)

To 4'-ethylbiphenylcarboxylic acid (20 mmol) dissolved in 50 mL dry DMF was added 25 mmol of triethylamine and the mixture was cooled in an ice bath, added 38.5 mmol of methyl chloroformate dropwise at 0°–5° C., and then stirred at room temperature for 15 minutes. The mixture was cooled to 0° C. again, and a cold solution of 38.5 mmol of sodium azide dissolved in a minimum amount of water (<8 mL) was added as rapidly as possible (in one portion if possible) at <5° C. The reaction mixture was stirred at 0° C. for 1 hour and poured into 500 mL of ice-water. The resulting precipitate was filtered while still cold (<10 min), washed with cold water and dried under a stream of nitrogen to give the crude 4'-ethylbiphenylcarbonyl azide. The azide was used in place of 4'-ethylbiphenylisocyanate for the subsequent reactions according to the procedures exactly paralleling those described previously for Examples 1 through 3 to give the desired product as a colorless solid, mp 223°–224° C.

By using the procedures described in Examples 113 and 114, the following compounds in Table VII were prepared or can be prepared.

TABLE VII

Ar—⟨phenyl⟩—N(oxazolidinone)—B

| Ex. | Ar | B | Isomer | m.p.(°C.) |
|---|---|---|---|---|
| 113 | 2',5'-diOHC₆H₃ | NHCOCH₃ | l | 227–228.5 |
| 114 | 4'-C₂H₅C₆H₄ | NHCOCH₃ | l | 223–224 |
| 115 | 4'-(CH₃)₂NC₆H₄ | NHCOCH₃ | dl | |
| 116 | 4'-(CH₃)₂N(O)C₆H₄ | NHCOCH₃ | dl | 125–127 |
| 117 | 4'-(9-fluorinon-2-yl) | NHCOCH₃ | l | 237.5–238.5 |
| 118 | 4'-(9-fluorinon-2-yl) | NHCOCH₃ | l | 214–221 |
| 119 | 3'-O₂NC₆H₄ | NHCOCH₃ | l | 140–141 |

TABLE VII-continued

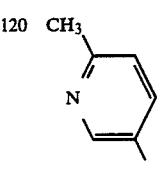

| Ex. | Ar | B | Isomer | m.p.(°C.) |
|---|---|---|---|---|
| 120 | 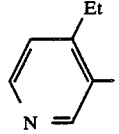 2-CH₃ pyridyl | NHCOCH₃ | dl | |
| 121 | 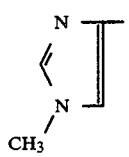 Et, CH₃ pyridyl | NHCOCH₃ | dl | |
| 122 | 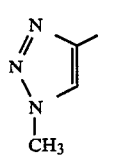 N-CH₃ imidazolyl | NHCOCH₃ | l | |
| 123 | 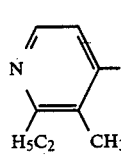 N-CH₃ triazolyl | NHCOCH₃ | l | |
| 124 | 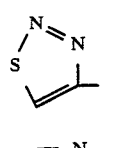 H₅C₂, CH₃ pyridyl | NHCOCH₃ | l | |
| 125 | 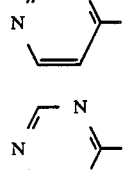 thiadiazolyl | NHCOCH₃ | l | |
| 126 | 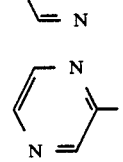 pyrazinyl | NHCOCH₃ | l | |
| 127 | 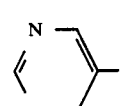 pyrimidinyl | NHCOCH₃ | l | |
| 128 | pyrazinyl | NHCOCH₃ | l | |
| 129 | 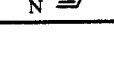 pyridazinyl | NHCOCH₃ | l | 209-211 |

EXAMPLE 130

Preparation of
(l)-N-[3-[4-(5-Isoxazolyl)phenyl]-2-oxooxazolidin-5-ylmethyl]acetamide (I, Ar=5—isoxazolyl, B=NHCOCH₃)

A mixture of (l)-N-[3-(4-acetylphenyl)-2-oxooxazolidin-5-ylmethyl]acetamide (500 mg, 1.8 mmol) in 2 mL of dimethoxyformamide was heated at 110° C. overnight (16 hours). Excess dimethoxyformamide was removed in vacuo and the residue was purified by flash column chromatography to give 328 mg (55%) of (l)-N-[3-(4-(3-dimethylamino-2-ethenylketo)phenyl)-2-oxooxazolidin-5-ylmethyl]acetamide as a white solid. mp 191°-192° C.; ¹H-NMR (CDCl₃) δ: 7.95 (d,J=7 Hz,2H), 7.83 (d,J=13 Hz,1H), 7.58 (d,J=7 Hz,2H), 6.50 (m,1H), 5.75 (d,J=13 Hz,1H), 4.83 (bs,1H), 4.12 (t,1H), 3.83 (dd,1H), 3.67 (m,2H), 3.17 (bs,3H), 3.00 (bs,3H), 2.05 (s,3H); MS: m/e 331.1537 (M+), calcd. for $C_{17}H_{21}N_3O_4$: 331.1530.

A solution of the above compound (325 mg, 0.98 mmol) in methanol (3 mL) was treated with hydroxylamine-O-sulfonic acid (125 mg, 1.08 mmol) at room temperature for 45 minutes. It was poured into saturated sodium bicarbonate solution. The resulting solid was collected and washed with water to give, after drying, 167 mg (57%) of the product as a white solid. mp 175°-178° C. (dec); ¹H-NMR (d₆-DMSO) δ: 8.63 (bs,1H), 8.28 (bs,1H), 7.92 (d,J=7 Hz,2H), 7.72 (d,J=7 Hz,2H), 7.00 (bs,1H), 4.77 (bs,1H), 4.20 (t,1H), 3.82 (t,1H), 3.43 (m,2H), 1.87 (s,3H); MS: m/e 301.1081 (M+), calcd. for $C_{15}H_{15}N_3O_4$: 301.1061.

EXAMPLE 131

Preparation of
(l)-[3-(4-(2-Methyl-4-thiazolyl)phenyl)-2-oxooxazolidin-5-ylmethyl]azide (I, Ar=2-methyl-4-thiazolyl, B=N₃)

A solution of (l)-5-azidomethyl-N-[3-(4-acetylphenyl-2-oxooxazolidin] (2.47 g, 9.5 mmol) in chloroform (30 mL) was treated with bromine (0.53 mL, 10.45 mmol) at room temperature for 15 minutes. The solvent was removed and the residue was taken up with 10% methanol/methylene chloride. The resulting solid was filtered off and the solvent of the filtrate was removed to afford the crude product which was purified by flash column chromatography to yield 2.15 g (68%) of the bromoacetyl compound.

¹H-NMR (CDCl₃) δ: 8.00 (d,J=7 Hz,2H), 7.67 (d,J=7 Hz,2H), 4.83 (m,1H), 4.40 (s,2H), 4.15 (t,1H), 3.93 (dd,1H), 3.70 (2dd,2H).

A mixture of the above bromoacetyl compound (200 mg, 0.59 mmol) and thioacetamide (55 mg, 0.7 mmol) in toluene (3 mL) was refluxed for six hours. The solvent was removed, the residue was diluted with 10% methanol/methylene chloride, washed with saturated brine and dried (Na₂SO₄). The crude product was purified by flash column chromatography to give 140 mg (76%) of the title compound, ¹H-NMR (d₆-acetone) δ: 8.00 (d,J=7 Hz,2H), 7.70 (d,J=7 Hz,2H), 7.67 (s,1H), 5.00 (m,1H), 4.30 (t,1H), 4.00 (dd,1H), 3.83 (m,2H), 2.73 (s,3H).

The title compound was converted into its acetamide compound (I, Ar=2-methyl-4-thiazolyl, B=NHCOCH₃) by the procedure described in U.S. Pat. No. 4,705,799.

By using the procedures described in Examples 130 and 131, the following compounds in Table VIII were prepared or can be prepared.

TABLE VIII

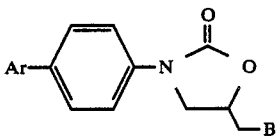

| Ex. | Ar | B | Isomer | m.p. (°C.) |
|---|---|---|---|---|
| 130 | 5-isoxazolyl | NHCOCH$_3$ | 1 | 175–178 |
| 131 | 2-methyl-4-thiazolyl | N$_3$ | 1 | NMR |
| 132 | 2-methyl-4-thiazolyl | NHCOCH$_3$ | 1 | 179–180 |
| 133 | 1H-pyrazol | NHCOCH$_3$ | 1 | 235–236 (dec) |
| 134 | 2-amino-4-thiazolyl | NHCOCH$_3$ | 1 | 171–174 (dec) |
| 135 | 2-amino-4-pyrimidinyl | NHCOCH$_3$ | 1 | 258 (dec) |
| 136 | 5-oxazolyl | NHCOCH$_3$ | 1 | 200 (dec) |

DOSAGE FORMS

The antibacterial agents of this invention can be administered by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration with standard pharmaceutical practice.

The dosage administered will, of course, vary depending upon known factors such as the pharmacodynamic characteristics of the particular agent, and its mode and route of administration; age, health, and weight of the recipient; nature and extent of symptoms; kind of concurrent treatment; frequency of treatment; and the effect desired. Usually, a daily dosage of active ingredient can be about 5 to 20 milligrams per kilogram of body weight. Ordinarily, when the more potent compounds of this invention are used, 5 to 15, and preferably 5 to 7.5 milligrams per kilogram per day, given in divided doses 2 to 4 times a day or in sustained release form, is effective to obtain desired results. These drugs may also be administered parenterally.

Projected therapeutic levels in humans should be attained by the oral administration of 5–20 mg/kg of body weight given in divided doses two to four times daily. The dosages may be increased in severe or life-threatening infections.

Dosage forms (compositions) suitable for internal administration contain from about 1.0 milligram to about 600 milligrams of active ingredient per unit. In these pharmaceutical compositions, the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelation capsules contain the active ingredient and powdered carriers, such as lactose, sucrose, manitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and, if necessary, buffer substances. Antioxidants such as sodium bisulfate, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, A. Osol, a standard reference text in this field.

Useful pharmaceutical dosage forms for administration of the compounds of this invention can be illustrated as follows:

CAPSULES

A large number of unit capsules are prepared by filling standard two-piece hard gelatin capsules each with 75 milligrams of powdered active ingredient, 150 milligrams of lactose, 24 milligrams of talc, and 6 milligrams of magnesium stearate.

SOFT GELATIN CAPSULES

A mixture of active ingredient in soybean oil is prepared and injected by means of a positive displacement pump into gelatin to form soft gelatin capsules containing 75 milligrams of the active ingredient. The capsules are washed and dried.

TABLETS

A large number of tablets are prepared by conventional procedures so that the dosage unit is 75 milligrams of active ingredient, 0.2 milligrams of colloidal silicon dioxide, 5 milligrams of magnesium stearate, 250 milligrams for microcrystalline cellulose, 11 milligrams of cornstarch and 98.8 milligrams of lactose. Appropriate coatings may be applied to increase palatability or delay absorption.

INJECTABLES

A parenteral composition suitable for administration by injection is prepared by stirring 1.5% by weight of active ingredient in 10% by volume propylene glycol and water. The solution is made isotonic with sodium chloride and sterilized.

SUSPENSIONS

An aqueous suspension is prepared for oral administration so that each 5 milliliters contain 75 milligrams of finely-divided active ingredient, 200 milligrams of sodium carboxymethyl cellulose, 5 milligrams of sodium benzoate, 1.0 grams of sorbitol solution, U.S.P., and 0.025 milliliters of vanillin.

UTILITY

Test results indicate that the compounds of this invention are biologically active against gram positive bacteria including multiple antibiotic resistant strains of staphylococci and streptococci. These compounds are potentially useful for the treatment of both human and animal bacterial infections including diseases of the respiratory, gastrointestinal, genito-urinary systems; blood; interstitial fluids; and soft tissues.

As shown in Table IX, compounds of Formula (I) exert an in vitro antibacterial effect. A standard microdilution method (*National Committee for Clinical Standards*. Tentative standard M7-T. Standard methods for dilution antimicrobial susceptibility tests for bacteria that grow aerobically. National Committee for Clinical Laboratory Standards, Villanova, Pa., 1982) with Mueller-Hinton broth is used to determine the 24-hour minimal inhibitory concentrations (MIC's) for test strains of *Staphylococcus aureus* and *Escherichia coli*.

The in vivo potency of these compounds is exemplified by the data summarized in Table X. Determinations of in vivo efficacy are performed by inoculating mice intraperitoneally with cultures of the infecting organism diluted to produce 100% mortality in control animals within twenty-four hours. The culture of *S. aureus* used to infect the animals was diluted to the required bacterial density using 5% aqueous hog gastric mucin. The compounds are dissolved or suspended in 0.25% aqueous Methocel ® (Methocel ®: Hydroxypropyl Methylcullulose, E15 Premium, Dow Chemical Company) for oral administration or sterile distilled water containing 5% dimethylsulfoxide (Fisher Scientific Company, Fairlawn, N.J.) for subcutaneous administration. The mice are dosed at one hour and at four hours post-infection. Mortality is recorded daily until test determination seven days post infection. The number of survivors in each treatment group on the seventh day after infection is used in the calculation of the $ED_{50}$, the dose of compound that protects 50% of the mice (Litchfield, J. T. and Wildoxon. A simulated method for evaluating dose-effect experiments. *J. Pharmacol Exp. Ther.*, 98:99–113, 1949).

TABLE IX

In Vitro Broth Microdilution Minimal Inhibitory Concentrations (MIC's)

| Example No. | Minimum Inhibitor, Concentration ($\mu$g/mL) | |
|---|---|---|
| | Staphylococccus aureus | Escherichia coli |
| 3 | 0.5 | >128 |
| 4 | 0.5 | >128 |
| 7 | 2 | >128 |
| 8 | <0.13 | >128 |
| 9 | <0.13 | >128 |
| 10 | 0.5 | >128 |
| 20 | 8 | >128 |
| 21 | <0.13 | >128 |
| 22 | 0.25 | >128 |
| 23 | 1 | >128 |
| 24 | 8 | >128 |
| 25 | 2 | >128 |
| 26 | 1 | >128 |
| 27 | 0.5 | >128 |
| 28 | <0.13 | >128 |
| 29 | 4 | >128 |
| 30 | 4 | >128 |
| 37 | 0.25 | >128 |
| 38 | 64 | >128 |
| 43 | 4 | >128 |
| 44 | 4 | >128 |
| 45 | 0.5 | >128 |
| 46 | 4 | >128 |
| 47 | 0.5 | >128 |
| 48 | <0.13 | >128 |
| 49 | 1 | >128 |
| 50 | 0.5 | >128 |
| 57 | 1 | >128 |
| 58 | 1 | >128 |
| 59 | 2 | >128 |
| 60 | 1 | >128 |
| 61 | 2 | >128 |
| 62 | 2 | >128 |
| 63 | 0.25 | >128 |
| 64 | 4 | >128 |
| 65 | 2 | >128 |
| 66 | 0.5 | >128 |
| 67 | 0.25 | >128 |
| 68 | 0.25 | >128 |
| 69 | 0.25 | >128 |
| 70 | 2 | >128 |
| 71 | 2 | >128 |
| 73 | 0.5 | >128 |
| 74 | 8 | >128 |
| 75 | <0.13 | >128 |
| 85 | <0.13 | >128 |
| 86 | 2 | >128 |
| 87 | 32 | >128 |
| 88 | <0.13 | >128 |
| 89 | 2 | >128 |
| 92 | 2 | >128 |
| 113 | 16 | >128 |
| 114 | 0.5 | >128 |
| 115 | 16 | >128 |
| 116 | 16 | >128 |
| 117 | 4 | >128 |
| 118 | 4 | >128 |
| 119 | <0.13 | >128 |
| 130 | 1 | >128 |
| 132 | 4 | >128 |
| 133 | 4 | >128 |
| 134 | 8 | >128 |
| 135 | 4 | >128 |
| 136 | 1 | >128 |

TABLE X

In Vivo Activity of Compounds Against *Staphylococcus Aureus* in an Acute Lethal Mouse Model

| Example No. | $ED_{50}$ (mg/kg) | |
|---|---|---|
| | Oral Administration | Subcutaneous Administration |
| 3 | 2.9 | 2 |
| 4 | 22 | 39.7 |
| 7 | NT | >90 |
| 8 | >90 | >90 |
| 9 | >90 | 16.8 |
| 10 | NT | NT |
| 20 | >90 | >90 |
| 21 | 44.7 | >90 |
| 22 | >90 | >90 |
| 23 | 17.3 | 24.3 |
| 24 | >90 | >90 |
| 25 | 13.9 | 5.8 |
| 26 | NT | NT |
| 27 | 6.6 | 7.6 |
| 28 | 52.6 | 30 |
| 29 | 16.1 | 9.8 |
| 30 | 16.1 | 9.8 |
| 37 | <1.2 | 0.6 |
| 38 | NT | >90 |
| 43 | 6.4 | 3.7 |
| 44 | 8.6 | 3.7 |
| 45 | NT | 13.9 |
| 46 | NT | 30 |
| 47 | NT | NT |

TABLE X-continued

In Vivo Activity of Compounds Against *Staphylococcus Aureus* in an Acute Lethal Mouse Model

| Example No. | ED$_{50}$ (mg/kg) | |
|---|---|---|
| | Oral Administration | Subcutaneous Administration |
| 48 | NT | NT |
| 49 | 65.2 | >90 |
| 50 | NT | 6.5 |
| 57 | 18 | 10 |
| 58 | 13.8 | 2 |
| 59 | 7 | 2.7 |
| 60 | 30 | 5.5 |
| 61 | 47.4 | 2.7 |
| 62 | 51.9 | 10 |
| 63 | >90 | >90 |
| 64 | 50 | 11 |
| 65 | NT | 4.3 |
| 66 | NT | NT |
| 67 | 4.5 | 30 |
| 68 | 2.2 | 0.7 |
| 69 | 4 | 1.2 |
| 70 | 17 | 10 |
| 71 | 51.9 | >90 |
| 73 | 11.8 | 5 |
| 74 | NT | 17.1 |
| 75 | NT | NT |
| 85 | 1.3 | 0.5 |
| 86 | NT | 15.5 |
| 87 | 16.1 | 9.8 |
| 88 | 1.6 | 0.5 |
| 89 | 2 | <3.3 |
| 92 | NT | NT |
| 113 | >90 | 68.3 |
| 114 | 8.1 | >100 |
| 115 | NT | NT |
| 116 | NT | 6.4 |
| 117 | NT | NT |
| 118 | NT | NT |
| 119 | 6.2 | 5 |
| 130 | 6 | 6 |
| 132 | NT | 17 |
| 133 | 22 | 22 |
| 134 | 56.5 | 47 |
| 135 | 68 | NT |
| 136 | 14.8 | 51.9 |

NT = Not Tested

What is claimed is:

1. An aryl benzene oxazolidinone of the formula

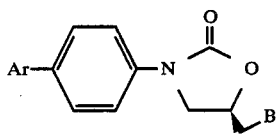
(I)

wherein, for the l, and mixtures of the d and l stereoisomers of the compound

Ar is

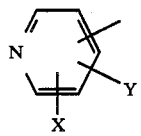

X independently is H, —NO$_2$, —S(O)$_n$R$_1$, —S(O)$_2$—N=S(O)$_p$R$_2$R$_3$,

—CONR$_5$R$_6$, 
$$-\overset{NR_7}{\underset{R_6}{\overset{\|}{C}}}-R_{23}, \quad -\overset{OR_8}{\underset{R_6}{\overset{|}{C}}}-R_{23}, \quad -\overset{O}{\overset{\|}{C}}R_{23},$$

$$R_6R_5N-(CH_2)_t-\overset{OR_8}{\underset{R_6}{\overset{|}{C}}},\ -CN,\ -OR_5,\ halogen,\ -NR_5R_6,$$

$$-\overset{R_5}{\underset{}{\overset{|}{N}}}COR_4,\ -\overset{R_5}{\underset{}{\overset{|}{N}}}S(O)_nR_4,\ -C_{23}(OR_{16})OR_{17},\ -\overset{NR_5R_{25}}{\underset{R_9}{\overset{|}{C}}}R_{23},\ alkyl$$

of 1 to 8 carbons optionally substituted with halogen, OH, =O other than at alpha position, S(O)$_n$R$_{24}$, or NR$_5$R$_6$, alkenyl of 2-5 carbons or cycloalkyl of 3-8 carbons;

R$_1$ is C$_1$-C$_4$ alkyl, optionally substituted with halogen, OH, CN, NR$_5$R$_6$ or CO$_2$R$_8$; C$_2$-C$_4$ alkenyl; —NR$_9$R$_{10}$; —N$_3$;

$$-NHCR_4;\ -NMCR_4;\overset{O}{\overset{\|}{}}\overset{O}{\overset{\|}{}}$$

—NG$_2$; —NR$_9$G—-NGM+;

R$_2$ and R$_3$ are independently C$_1$-C$_2$ alkyl;

R$_4$ is alkyl of 1-4 carbons, optionally substituted with halogen;

R$_5$ and R$_6$ are independently H, alkyl of 1-8 carbons, cycloalkyl of 3-8 carbons, —(CH$_2$)$_t$OR$_8$, —(CH$_2$)$_t$R$_{11}$R$_{11a}$, or —O(CH$_2$)$_t$NR$_{11}$R$_{11a}$;

R$_7$ is —NR$_5$R$_6$, —OR$_5$ or $$\overset{O}{\overset{\|}{NHCR_5;}}$$

R$_8$ is H or alkyl of 1-4 carbons;

R$_9$ is H, C$_1$-C$_4$ alkyl or C$_3$-C$_8$ cycloalkyl;

R$_{10}$ is H, C$_1$-C$_4$ alkyl, C$_2$-C$_4$ alkenyl, C$_3$-C$_4$ cycloalkyl, —OR$_8$ or NR$_{11}$R$_{114}$;

R$_{11}$ and R$_{114}$ are independently H or C$_1$-C$_4$ alkyl;

G is Cl, Br or I;

Y independently is H, F, Cl, Br, OR$_8$, alkyl of 1-3 carbons, or NO$_2$; or

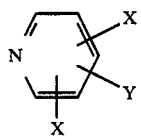

is:

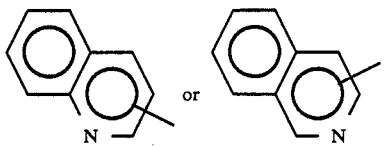

M is a physiologically acceptable cation;

n is 0, 1 or 2;
p is 0 or 1;
r is 4 or 5;
t is 1, 2 or 3;
B is —NH$_2$,

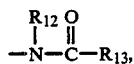

—N—S(O)$_u$R$_{14}$, or N$_3$;
R$_{12}$ is H, C$_1$-C$_{10}$ alkyl or C$_3$-C$_8$ cycloalkyl;
R$_{13}$ is H; C$_1$-C$_4$ alkyl optionally substituted with halogen, C$_2$-C$_4$ alkenyl; C$_3$-C$_4$ cycloalkyl; phenyl; —CH$_2$OR$_{15}$; —CH(OR$_{16}$)OR$_{17}$; —CH$_2$S(O)$_v$R$_{14}$;

—OR$_{18}$; —SR$_{14}$; —CH$_2$N$_3$; an aminoalkyl group derived from an α-amino acid selected from the group consisting of glycine, L-alanine, L-cysteine, L-proline, and D-alanine; —NR$_{19}$R$_{20}$; or —C(CH$_2$)R$_{21}$R$_{22}$;
R$_{14}$ is C$_1$-C$_4$ alkyl, optionally substituted with halogen;
R$_{15}$ is H or C$_1$-C$_4$ alkyl, optionally substituted with halogen;
R$_{16}$ and R$_{17}$ are independently C$_1$-C$_4$ alkyl or, taken together are —(CH$_2$)$_m$—;
R$_{18}$ is C$_1$-C$_4$ alkyl or C$_7$-C$_{11}$ aralkyl;
R$_{19}$ and R$_{20}$ are independently H or C$_1$-C$_2$ alkyl;
R$_{21}$ and R$_{22}$ are independently H, C$_1$-C$_4$ alkyl, C$_3$-C$_6$ cycloalkyl, phenyl;
u is 1 or 2;
v is 0, 1 or 2;
m is 2 or 3;
s is 2, 3, 4 or 5;
R$_{23}$ is H, alkyl of 1-8 carbons optionally substituted with halogen. cycloalkyl of 3-8 carbons, alkyl of 1-4 carbons substituted with one or more of —S(O)$_n$R$_{24}$, —OR$_8$,

or —NR$_5$R$_6$; or alkenyl of 2-5 carbons optionally substituted with CHO or CO$_2$R$_8$;
R$_{24}$ is alkyl of 1-4 carbons or cycloalkyl of 3-8 carbons; and
R$_{25}$ is R$_6$ or NR$_5$R$_6$;
or a pharmaceutically suitable salt thereof.

2. An oxazolidinone of claim 1 wherein B is

where R$_{13}$ IS H, CH$_3$, —OR$_{18}$, CH$_2$Cl, CH$_2$OH, or CH$_2$OCH$_3$.

3. An oxazolidinone of claim 2 wherein B is

4. An oxazolidinone of claim 1 wherein Ar is

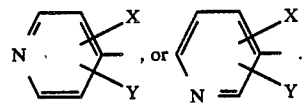

5. An oxazolidinone of claim 4 wherein Y is H.
6. An oxazolidinone of claim 5 wherein X is H, alkyl of 1-5 carbon atoms, —S(O)$_n$CH$_3$ where n is 0, 1 or 2,

—OR$_5$, —CH$_2$NR$_5$R$_6$, R$_6$R$_5$N(CH$_2$)$_2$ CH(OH)—, or —CN.

7. An oxazolidinone of claim 3 wherein Ar is

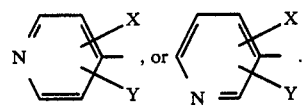

8. An oxazolidinone of claim 7 wherein Y is H.
9. An oxazolidinone of claim 8 wherein X is H, alkyl of 1-5 carbon atoms, —S(O)$_n$CH$_3$ where n is 0, 1 or 2,

—OR$_5$, —CH$_2$NR$_5$R$_6$, R$_6$R$_5$N(CH$_2$)$_2$ CH(OH)—, or —CN.

10. The oxazolidinone of claim 7 which is (l)-N-[3-(4-(4'-pyridyl)phenyl)-2-oxooxazolidin-5-ylmethyl]acetamide, hydrochloride.

11. The oxazolidinone of claim 7 which is (l)-N-[3-(4-(3'-pyridyl)phenyl)-2-oxooxazolidin-5-ylmethyl]acetamide, hydrochloride.

12. A pharmaceutical composition consisting essentially of a suitable pharmaceutical carrier and an effective amount of a compound of claim 1.

13. The oxazolidinone of claim 7 which is (l)-N-[3-(4-(4'-methyl-3'-pyridyl)phenyl)-2-oxooxazolidin-5-ylmethyl] acetamide.

14. A pharmaceutical composition consisting essentially of a suitable pharmaceutical carrier and an effective amount of a compound of claim 2.

15. A pharmaceutical composition consisting essentially of a suitable pharmaceutical carrier and an effective amount of a compound of claim 3.

16. A pharmaceutical composition consisting essentially of a suitable pharmaceutical carrier and an effective amount of a compound of claim 4.

17. A pharmaceutical composition consisting essentially of a suitable pharmaceutical carrier and an effective amount of a compound of claim 5.

18. A pharmaceutical composition consisting essentially of a suitable pharmaceutical carrier and an effective amount of a compound of claim 6.

19. A pharmaceutical composition consisting essentially of a suitable pharmaceutical carrier and an effective amount of a compound of claim 7.

20. A pharmaceutical composition consisting essentially of a suitable pharmaceutical carrier and an effective amount of a compound of claim 8.

21. A pharmaceutical composition consisting essentially of a suitable pharmaceutical carrier and an effective amount of a compound of claim 9.

22. A pharmaceutical composition consisting essentially of a suitable pharmaceutical carrier and an effective amount of the compound of claim 10.

23. A pharmaceutical composition consisting essentially of a suitable pharmaceutical carrier and an effective amount of the compound of claim 11.

24. A method of treating a bacterial infection in a mammal comprising: administering to the mammal an antibacterial amount of a compound of claim 1.

25. A method of treating a bacterial infection in a mammal comprising: administering to the mammal an antibacterial amount of a compound of claim 7.

26. A method of treating a bacterial infection in a mammal comprising: administering to the mammal an antibacterial amount of a compound of selected from the group consisting of:
(a) (l)-N-[3-(4-(4'-pyridyl)phenyl-2-oxooxazolidin-5-ylmethyl]acetamide, hydrochloride;
(b) (l)-N-[3-(4-(3'-pyridyl)phenyl-2-oxooxazolidin-5-ylmethyl]acetamide, hydrochloride; or
(c) (l)-N-[3-(4-4'-methyl-3'-pyridyl)phenyl-2-oxooxazolidin-5-ylmethyl]acetamide.

* * * * *